(12) United States Patent
Peters et al.

(10) Patent No.: US 8,401,641 B2
(45) Date of Patent: *Mar. 19, 2013

(54) TREATMENT OF CARDIAC ARRHYTHMIA BY MODIFICATION OF NEURONAL SIGNALING THROUGH FAT PADS OF THE HEART

(75) Inventors: Nicholas S. Peters, Farnham Common Bucks (GB); Mark Maciejewski, Edina, MN (US); Todor N. Mazgalev, Cleveland, OH (US)

(73) Assignee: CardioPolymers, Inc., Laguna Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/291,082

(22) Filed: Nov. 7, 2011

(65) Prior Publication Data

US 2012/0053510 A1 Mar. 1, 2012

Related U.S. Application Data

(60) Division of application No. 11/803,673, filed on May 15, 2007, now Pat. No. 8,073,538, and a continuation-in-part of application No. 10/989,227, filed on Nov. 15, 2004, now abandoned.

(60) Provisional application No. 60/800,566, filed on May 15, 2006, provisional application No. 60/550,076, filed on Mar. 4, 2004, provisional application No. 60/550,185, filed on Mar. 3, 2004, provisional application No. 60/523,848, filed on Nov. 20, 2003, provisional application No. 60/519,588, filed on Nov. 13, 2003.

(51) Int. Cl.
*A61N 1/00* (2006.01)

(52) U.S. Cl. ............ 607/14; 607/3; 604/522; 424/78.01

(58) Field of Classification Search ........................ None
See application file for complete search history.

(56) References Cited

U.S. PATENT DOCUMENTS

| | | |
|---|---|---|
| 4,874,368 A | 10/1989 | Miller et al. |
| 5,709,854 A | 1/1998 | Griffith-Cima et al. |
| 5,951,484 A | 9/1999 | Hoium et al. |
| 6,059,726 A | 5/2000 | Lee et al. |
| 6,136,334 A | 10/2000 | Veigas et al. |
| 6,151,525 A | 11/2000 | Soykan et al. |
| 6,292,695 B1 | 9/2001 | Webster, Jr. et al. |
| 6,425,918 B1 | 7/2002 | Shapiro et al. |
| 6,454,739 B1 | 9/2002 | Chang |

(Continued)

FOREIGN PATENT DOCUMENTS

| | | |
|---|---|---|
| WO | 9915211 A1 | 4/1999 |
| WO | 9948545 A1 | 9/1999 |

(Continued)

OTHER PUBLICATIONS

European Patent Office, Minutes of the Oral Proceedings Before the Examining Division on Dec. 7, 2011, European Patent Application No. 04 819 131.6, Dec. 27, 2011, 20 pages.

(Continued)

*Primary Examiner* — Carl H Layno
*Assistant Examiner* — Paula J Stice
(74) *Attorney, Agent, or Firm* — David H. Carroll

(57) ABSTRACT

To control cardiac arrhythmias such as atrial fibrillation postoperatively, various non-ablative agents include polymers, fibroblasts, neurotoxins, and growth factors are introduced into one or more cardiac fat pads into the atrioventricular nodal fat pad in proximity to the autonomic ganglia therein. Any desired technique may be used for introducing the agent, including injection. The sinoatrial nodal fat pad target site and the atrioventricular nodal fat pad target site are identified using a stimulator, which may have electrodes coupled thereto or which may coupled to electrodes built into a delivery system.

17 Claims, 20 Drawing Sheets

U.S. PATENT DOCUMENTS

| | | | |
|---|---|---|---|
| 6,544,503 | B1 | 4/2003 | Vanderhoff et al. |
| 6,630,457 | B1 | 10/2003 | Aeschlimann et al. |
| 6,696,575 | B2 | 2/2004 | Schmidt et al. |
| 6,699,471 | B2 | 3/2004 | Radice et al. |
| 6,767,544 | B2 | 7/2004 | Brooks et al. |
| 6,932,804 | B2 | 8/2005 | Lee |
| 8,073,538 | B2 | 12/2011 | Peters et al. |
| 2003/0104568 | A1 | 6/2003 | Lee |
| 2004/0002740 | A1 | 1/2004 | Lee |
| 2004/0005295 | A1 | 1/2004 | Lee et al. |
| 2004/0106896 | A1 | 6/2004 | Lee et al. |
| 2004/0143238 | A1 | 7/2004 | Lee |
| 2004/0242469 | A1 | 12/2004 | Lee et al. |
| 2005/0003010 | A1 | 1/2005 | Cohen et al. |
| 2005/0010263 | A1 | 1/2005 | Schauerte |
| 2005/0119704 | A1 | 6/2005 | Peters et al. |
| 2006/0083717 | A1 | 4/2006 | Lee et al. |
| 2006/0200207 | A1 | 9/2006 | Thrope et al. |
| 2006/0200219 | A1 | 9/2006 | Thrope et al. |
| 2008/0004662 | A1 | 1/2008 | Peters et al. |

FOREIGN PATENT DOCUMENTS

| | | | |
|---|---|---|---|
| WO | 9960923 | A1 | 12/1999 |
| WO | 0134088 | A2 | 5/2001 |
| WO | 03026480 | A2 | 4/2003 |
| WO | 03094855 | A1 | 11/2003 |
| WO | 03095016 | A1 | 11/2003 |
| WO | 2004050013 | A2 | 6/2004 |
| WO | 2004050013 | A3 | 6/2004 |
| WO | 2005049111 | A2 | 6/2005 |
| WO | 2007133784 | A2 | 11/2007 |

OTHER PUBLICATIONS

Australian Patent Office, Office Action: Australian Patent Application No. 2007249682, Mar. 5, 2012, 3 pages.

European Patent Office, Extended European Search Report, European Patent Application No. 11 183 428.9, Jun. 20, 2012, 10 pages.

Quan, Kara J., et al., Identification and Characterization of Atrioventricular Parasympathetic Innervation in Humans, Journal of Cardiovascular Electrophysiology, vol. 13, No. 8, Aug. 2002, pp. 735-739.

R&D Systems Inc., 1996 Catalog: Fibroblast Growth Factor 9, 2 pages, (Retrieved from the Internet <URL: http://www.rndsystems.com/asp/g_sitebuilder.asp?bBodyOnly=1&bodyID =199).

R&D Systems Inc., 2001 Catalog: Fibroblast Growth Factors, 9 pages, (Retrieved from the Internet <URL: http://www.rndsystems.com/asp/g_SiteBuilder.asp?bBodyOnly=1&BodyID =308).

Saltman, Adam E., New Onset postoperative atrial fibrillation: A riddle wrapped in a mystery inside an enigma, The Journal of Thoracic and Cardiovascular Surgery, vol. 127, No. 2, Feb. 2004, pp. 311-313.

Scherlag, Benjamin, J., et al., Stimulation of the 'Sino-Atrial' Fat Pad Converts Focal Pulmonary Vein Firing Into Atrial Fibrillation in the Dog Heart, Circulation, vol. 108, No. 17, Oct. 2003, 1 page.

Sierra, David H., Fibrin Sealant Adhesive Systems: A Review of Their Chemistry, Material Properties and Clinical Applications, Journal of Biomaterials Applications, vol. 7, No. 4, Apr. 1993, pp. 309-352.

Smith, F.M, Extrinsic imputs to intrinsic neurons in the porcine heart in vitro, Am J Physiol Regul Integr Comp Physiol, vol. 276, Feb. 1999, R455-R467.

Steinberg, Jonathan, Editorial Comment: Postoperative Atrial Fibrillation: A Billion-Dollar Problem, Journal of the American College of Cardiology, vol. 43, No. 6, Mar. 2004, pp. 1001-1003.

Symphony Medical, Inc., Reply to Office Action: Chinese Patent Application No. 200480033455.8, Apr. 15, 2008, 31 pages.

Symphony Medical, Inc., Reply to Office Action: Chinese Patent Application No. 200480033455.8, Feb. 26, 2009, 14 pages.

Symphony Medical, Inc., Reply to Office Action: European Patent Application No. 04 819 131.6, Oct. 26, 2009, 26 pages.

Symphony Medical, Inc., Reply to Office Action: European Patent Application No. 04 819 131.6, Mar. 25, 2010, 62 pages.

Symphony Medical, Inc., Reply to Office Action: European Patent Application No. 04 819 131.6, Mar. 10, 2011, 19 pages.

Symphony Medical, Inc., Reply to the Written Opinion of the ISA/US Pursuant to Article 34: International Patent Application No. PCT/US2004/38128, May 12, 2006, 4 pages.

Tsuboi, Masato, et al., Botulinum Neurotoxin A Blocks Cholinergic Ganglionic Neurotransmission in the Dog Heart, Jpn. J. Pharmacol, vol. 89, 2002, pp. 249-254.

Tsuboi, Masato, et al, Inotropic, chronotropic, and dromotropic effects mediated via parasympathetic ganglia in the dog heart, Am J Physiol Heart Circ Physiol, vol. 279, Sep. 2000, H1201-H1207.

United States Patent and Trademark Office, Office Action: U.S. Appl. No. 10/989,227, Aug. 2, 2006, 14 pages.

United States Patent and Trademark Office, Office Action: U.S. Appl. No. 10/989,227, Jan. 5, 2007, 10 pages.

United States Patent and Trademark Office: Notice of Allowance and Fee(s) Due: U.S. Appl. No. 11/803,673, Jun. 4, 2010, 37 pages.

United States Patent and Trademark Office: Notice of Allowance and Fee(s) Due: U.S. Appl. No. 11/803,673, Aug. 8, 2011, 22 pages.

Wallick, Don W., et al., Selective AV nodal vagal stimulation improves hemodynamics during acute atrial fibrillation in dogs, Am J Physiol Heart Circ Physiol 281, 2001, pp. H-1490-H1497.

Wilber, David J., et al., Vagal Stimulation and Atrial Fibrillation: Experimental Models and Clinical Uncertainties, Journal of Cardiovascular Electrophysiology, vol. 13, No. 12, Dec. 2002, pp. 1280-1282.

Zhang, MD, Youhua, et al., Achieving regular slow rhythm during atrial fibrillation without atrioventricular nodal ablation: Selective vagal stimulation plus ventricular pacing, Heart Rhythm, vol. 4, 2004, pp. 469-475.

Zhang, MD, Youhua, et al., Chronic Atrioventricular Nodal Vagal Stimulation: First Evidence for Long-Term Ventricular Rate Control in Canine Atrial Fibrillation Model, Circulation, Nov. 8, 2005, pp. 2904-2911.

Symphony Medical, Inc., Reply to Noting of Loss or Rights: European Patent Application No. 07 794 897.4, Jul. 15, 2010, 12 pages.

European Patent Office, Communication Pursuant to Article 94(3) EPC, European Patent Application No. 07 794 897.4, Jul. 12, 2012, 5 pages.

Allergan, Inc., Botox: Mechanism of Action, Nov. 12, 2004 (date is when retrieved from the Internet site http://www.botox.com/site/professionals/product_info/mechanism_of_action.asp), 10 pages.

Armour, J. Andrew, et al., Gross and Microscopic Anatomy of the Human Intrisic Cardiac Nervous System, The Anatomical Record, vol. 247, 1997, pp. 289-298.

Baxter AG, Duplocath Application Catheter, 1999, 2 pages.

Baxter Healthcare Corporation, CoSeal Surgical Sealant: Use Instructions, Mar. 2003, 2 pages.

Campbell, Patrick K., et al., Evaluation of Absorbable Surgical Sealants: In vitro Testing, White Paper, 2005, 4 pages.

Carlson, Mark D., et al., Selective Stimulation of Parasympathetic Nerve Fibers to the Human Sinoatrial Node, Circulation, vol. 85, No. 4, Apr. 1992, pp. 1311-1317.

Chinese Patent Office, Office Action, Chinese Patent Application No. 200480033455.8, Nov. 30, 2007, 7 pages.

Chinese Patent Office, Office Action, Chinese Patent Application No. 200480033455.8, Dec. 19, 2008, 9 pages.

Christman, Karen L., et al., Injectable Fibrin Scaffold Improves Cell Transplant Survival, Reduces Infarct Expansion, and Induces Neovasculature Formation in Ischemic Myocardium, Journal of the American College of Cardiology, vol. 44, No. 3, Aug. 2004, 8 pages.

Cummings, Jennifer E., et al., Preservation of the Anterior Fat Pad Paradoxically Decreases the Incidence of Postoperative Atrial Fibrillation in Humans, Journal of the American College of Cardiology, vol. 43, No. 6, Mar. 2004, pp. 994-1000.

Dickneite, Gerhard, et al., A comparison of fibrin sealants in relation to their in vitro and in vivo properties, Thrombosis Research, vol. 112, 2003, pp. 73-82.

European Patent Office, Office Action: European Patent Application No. 04 819 131.6, Sep. 8, 2009, 4 pages.

European Patent Office, Office Action: European Patent Application No. 04 819 131.6, Nov. 20, 2009, 4 pages.

European Patent Office, Supplementary European Search Report: European Patent Application No. 04 819 131.6, Jun. 9, 2009, 3 pages.
European Patent Office, Office Action: European Patent Application No. 04 819 131.6, Nov. 9, 2011, 4 pages.
European Patent Office, Extended European Search Report: European Patent Application No. 07 794 897.4, May 27, 2009, 7 pages.
Gospodarowicz, Denis, Fibroblast Growth Factor Chemical Structure and Biologic Function, Clinical Orthopedics and Related Research, No. 257, Aug. 1990, pp. 231-248.
Hirose, Masamichi, et al., Partial Vagal Denervation Increases Vulnerability to Vagally Induced Atrial Fibrillation, Journal of Cardiovascular Electrophysiology, vol. 13, No. 12, Dec. 2002, pp. 1272-1279.
Hoffmann, P. et al., Protection from reperfusion-induced arrhythmias by polyethylene glycol 600, J. Pharm. Pharmacol., vol. 45, No. 12, 1993, pp. 1093-1095.
International Preliminary Examining Authority/US, International Preliminary Report on Patentability: International Patent Application No. PCT/US04/38128, Aug. 9, 2006, 3 pages.
Iqbal, Yasmine, What's New in Wound Closures, Outpatient Surgery Magazine, Oct. 2002, 2 pages.
International Searching Authority/US, International Search Report: International Patent Application No. PCT/US04/38128, Feb. 16, 2006, 2 pages.
International Searching Authority/US, International Search Report: International Patent Application No. PCT/US07/11647, Nov. 13, 2007, 2 pages.
International Searching Authority/US, Written Opinion of the International Searching Authority: International Patent Application No. PCT/US04/38128, Feb. 16, 2006, 3 pages.
International Searching Authority/US, Written Opinion of the International Searching Authority, International Patent Application No. PCT/US07/11647, Nov. 13, 2007, 5 pages.
Jessurun, Emile R. et al., Mitral valve surgery and atrial fibrillation: is atrial fibrillation surgery also needed?, Eur J Cardiothoracic Surgery, vol. 17, 2000, p. 530 (Abstract).
Japanese Patent Office, Office Action: Japanese Patent Application No. 2006-539975, Sep. 2, 2009, 2 pages.
Kong, Hyun-Joon, et al., Controlling Material Properties of Ionically Cross-Linked Alginate Hydrogels by Varying Molecular Weight Distribution, Mat. Res. Soc. Symp. Proc., vol. 711, 2002, pp. GG5.7.1-GG5.7.4.
Lazzara, Ralph, et al., Selective In Situ Parasympathetic Control of the Canine Sinoatrial and Atrioventricular Nodes, Circulation Research, vol. 32, Mar. 1973, pp. 393-401.
Leung, Jacqueline M., et al., Impairment of left atrial function predicts post-operative atrial fibrillation after coronary artery bypass graft surgery, European Heart Journal, vol. 25, 2004, pp. 1836-1844.
Maciejewski, Mark et al., Post-Operative Control of Cardiac Ventricular Rate During Atrial Fibrillation by Vagal Stimulation at a Fat Pad of the Heart: U.S. Appl. No. 60/738,677, filed Nov. 21, 2005, 14 pages.
Marrouche, MD, Nassir F., Temporary Modification of the Epicardial Fat Pads in Patients Undergoing Low to Moderate Risk Open Heart Surgery: Safety and Efficacy of a Novel Approach for Lowering the Incidence of Post Operative Atrial Fibrillation, Heart Rhythm, vol. 3, No. 5, May 2006, pp. S148-S149 (abstract).
McGuirt, A. S., et al., Autonomic interactions for control of atrial rate are maintained after SA nodal parasympathectomy, Am. J. Physiol. 272 (Heart Circ. Physiol. 41), 1997, H2525-H2533.
Melo, MD, J., et al., Ventral cardiac denervation reduces the incidence of atrial fibrillation after coronary artery bypass grafting, The Journal of Thoracic and Cardiovascular Surgery, vol. 127, No. 2, Feb. 2004, pp. 511-516.
Moulton, Linda C., A Minimally Invasive Approach to the Treatment of Atrial Fibrillation: The Mini-Maze, EP Lab Digest, vol. 5, No. 11, Nov. 2005, pp. 1-6 & 8.
NovaMatrix, Sodium Hyaluronate Pharma Grade 200, Product Specification Bulletin, 2002, 2 pages.
O'Donnell, Sean D., et al., Evaluation of a New Hydrogel Vascular Sealant: In-vitro and In-vivo Test Results, White Paper, 2005, 4 pages.
Oz, Mehmet C., et al., Controlled Clinical Trial of a Novel Hemostatic Agent in Cardiac Surgery, Ann Thorac Surg, vol. 69, 2000, pp. 1376-1382.
Page, P., et al., Neurally Induced Atrial Fibrillation: Differences Between Stimulation of the Vagal Nerve and a Discrete Intrapericardial Nerve, Feb. 17, 2005 (date is when retrieved from the Internet site http://www.pulsus.com/ccc2004/abs/a152.htm), 1 page.
Pappone, Carlo, et al., Pulmonary Vein Denervation Enhances Long-Term Benefit After Circumferential Ablation of Paroxysmal Atrial Fibrillation, Circulation, vol. 109, 2004, 8 pages.
Pauza, Dainius H., et al., Morphology, Distribution, and Variability of the Epicardiac Neural Ganglionated Subplexuses in the Human Heart, The Anatomical Record, vol. 259, 2000, pp. 353-382.
Peters, Nicholas et al., Method to Cure Atrial Fibrillation by Modifying Local Autonomic Supply: U.S. Appl. No. 60/523,848, filed Nov. 30, 2003, 6 pages.
Peters, Nicholas et al., Method to Control Ventricular Rate: U.S. Appl. No. 60/519,588, filed Nov. 13, 2003, 6 pages.
Peters, Nicholas et al., Post-Operative Control of Cardiac Arrhythmia by Modification of Neuronal Conduction in the Fat Pads of the Heart: U.S. Appl. No. 60/800,566, filed May 15, 2006, 71 pages.
Peters, Nicholas et al., Preliminary Amendment: U.S. Appl. No. 11/803,673, Oct. 31, 2007, 21 pages.
Peters, Nicholas et al., Reply to Office Action, U.S. Appl. No. 10/989,227, Nov. 2, 2006, 24 pages.
Peters, Nicholas et al., Treatment of Cardiac Arrhythmias With Neurotoxins: U.S. Appl. No. 60/550,076, filed Mar. 4, 2004, 14 pages.
Peters, Nicholas et al., Treatment of Cardiac Arrhythmias With Neurotoxins: U.S. Appl. No. 60/550,185, filed Mar. 3, 2004, 14 pages.
Platt, MD, Marc, et al., Identification and Ablation of Pulmonary Vein Ganglia (Fat Pad): Atrial Fibrillation Substrate alteration as a Guide to Successful Radiofrequency Balation of Persistent Atrial Fibrillation, PACE, vol. 26, No. 4, Apr. 2003, p. 1117.

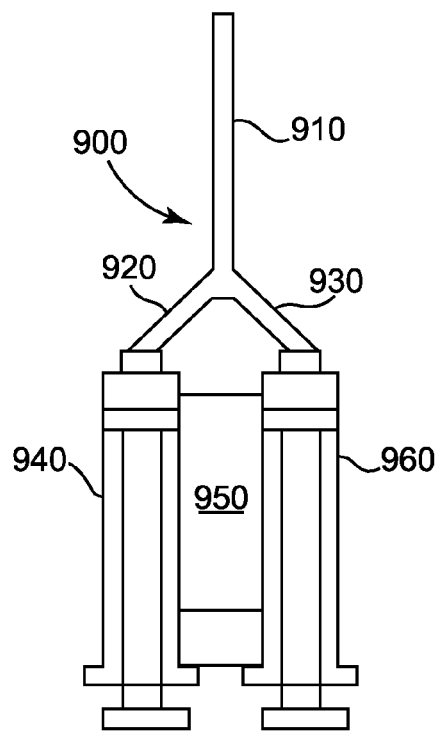 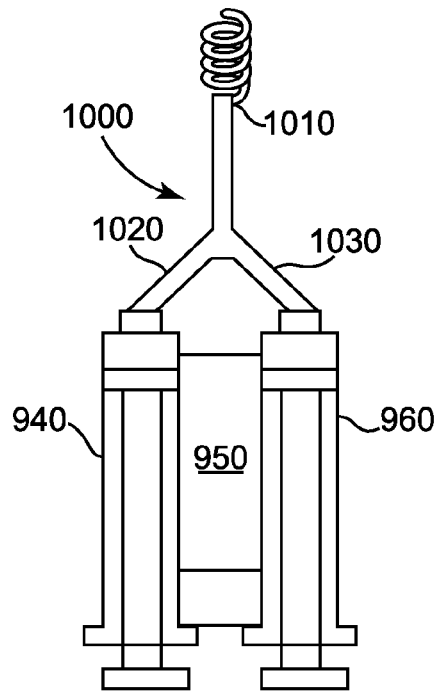
Fig. 9    Fig. 10
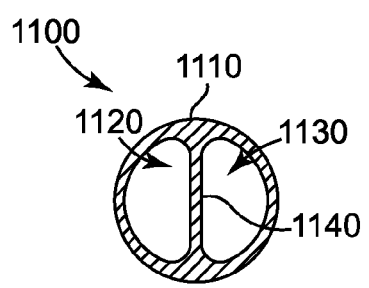 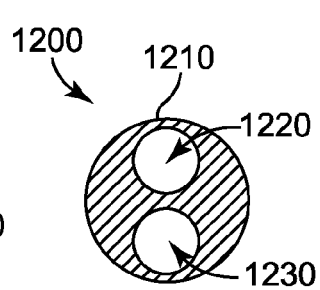 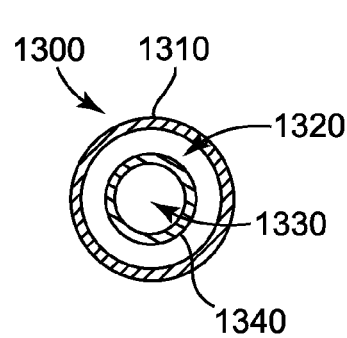
Fig. 11    Fig. 12    Fig. 13

BEFORE FIBRIN GLUE INJECTION

IMMEDIATELY AFTER FIBRIN GLUE INJECTION

BEFORE FIBRIN GLUE INJECTION

IMMEDIATELY AFTER FIBRIN GLUE INJECTION

INCIDENCE OF POST-OP AF
CLINICAL PERSPECTIVE AND CONTRAST

| | SYMPHONY #04-001 | | MELO. VENT. DENERV. | | GOMES SOTALOL | |
|---|---|---|---|---|---|---|
| | # | % | TREAT | CONTROL | SOTALOL | CONTROL |
| "POST-OP" AF REQUIRING INTERVENTION (96 HOURS) | 0/20 | 0% | 6% | 25% | 5% | 18% |
| AF AT DISCHARGE | 0/20 | 0% | nr | nr | nr | nr |
| AF WITHIN 30 DAYS (> 30 MIN. OR REQ. INTERVENTION) | 2/20 | 10% | nr | nr | nr | nr |
| PAROXYSMAL AF OF ANY DURATION POST-OP (96 HOURS) | 5/20 | 25% | nr | nr | 8% | 20% |

Fig. 27

TREATMENT OF CARDIAC ARRHYTHMIA BY MODIFICATION OF NEURONAL SIGNALING THROUGH FAT PADS OF THE HEART

CROSS-REFERENCE TO RELATED APPLICATIONS

This application is a divisional of U.S. patent application Ser. No. 11/803,673 now U.S. Pat. No. 8,073,538 filed May 15, 2007; which claims the benefit of U.S. Provisional Patent Application Ser. No. 60/800,566 filed May 15, 2006; and U.S. patent application Ser. No. 11/803,673 filed May 15, 2007 also is a continuation-in-part of U.S. patent application Ser. No. 10/989,227 filed Nov. 15, 2004 now abandoned, which claims the benefit of U.S. Provisional Patent Application Ser. No. 60/519,588 filed Nov. 13, 2003, U.S. Provisional Patent Application Ser. No. 60/523,848 filed Nov. 20, 2003, U.S. Provisional Patent Application Ser. No. 60/550,185 filed Mar. 3, 2004, and U.S. Provisional Patent Application Ser. No. 60/550,076 filed Mar. 4, 2004, all of which are incorporated herein in their entirety by reference thereto.

BACKGROUND OF THE INVENTION

1. Field of the Invention

The present invention relates to the treatment of medical conditions associated with the heart, and more particularly to treatment of cardiac arrhythmia by modification of neuronal signaling through one or more of the fat pads of the heart, and more particularly to treatment of post-operative atrial fibrillation by temporary modification of neuronal signaling through the atrioventricular and sinoatraial nodal fat pads of the heart.

2. Description of the Related Art

The autonomic nervous system (ANS) is divided into sympathetic and parasympathetic systems. Neural control of the heart is dependent on the levels of activity of the sympathetic and parasympathetic neurons and the interactions that occur between them. As disclosed in McGuirt, A. S., Autonomic interactions for control of atrial rate are maintained after SA nodal parasympathectomy, Am. J. Physiol. 272 (Heart Circ. Physiol. 41), 1997, H2525-H2533, for control of regional cardiac function, both pre- and post-junctional interactions occur between the separate autonomic projections to the heart, particularly at the end-organ target sites such as the SA node, the AV node, and contractile elements of the atria and ventricles. The sympathetic system increases the heart rate and ventricular contraction, dilates the blood vessels in skeletal muscles, constricts blood vessels in the skin and guts, increases blood sugar level, stimulates sweating, dilates the pupils, inhibits activities of the guts and gastric secretion. The parasympathetic system is more active at rest, having in general anabolic effects. For example, it slows down the heart rate, constricts the pupils, increases gastric secretion and intestinal motility.

The autonomic nervous system is formed from nerve cells or neurons, which receive, process, initiate and transmit messages through various signaling mechanisms. A neuron may terminate at one of three structures: a muscle, a gland, or another neuron. When a neuron terminates on a muscle or a gland, the neuron is said to "innervate" the structure. However, when two neurons join together, as they do within, for example, ganglionated plexsus of the nervous system, the junction between them is known as a "synapse." Typically, a synapse involves a junction between an axon terminal of one neuron, which is referred to as the presynaptic neuron, and the dendrites or cell body of a second neuron, which is referred to as postsynaptic neuron. The dendrites and to a lesser extent the cell body of most neurons receive thousands of synaptic inputs, which are axon terminals from many other neurons. The grand postsynaptic potential depends on the sum of the activities of all presynaptic inputs.

The heart is formed from muscle cells that display pacemaker activity, which is to say that the heart initiates its own action potentials without any external influence. Cardiac cells are interconnected by gap junctions that enhance the spread of action potentials through the heart. In the normal physiologic process, heart conduction moves from cell to cell, from the sinoatrial ("SA") node to the atrioventricular ("AV") node, and from the atrium to the ventricles. Although the heart like many other organs is innervated by the autonomic nervous system, the role of the autonomic nervous system is essentially to modify the rate and strength of contraction.

Cardiac arrhythmias are abnormal conditions associated with the various chambers and other structures of the heart. Atrial fibrillation ("AF") is the most frequently occurring sustained cardiac arrhythmia, particularly among the elderly and among patients with organic heart disease, as well as among patients recovering from coronary artery bypass graft ("CABG") surgery; see Steinberg, Jonathan S., Postoperative Atrial Fibrillation: A Billion-Dollar Problem, Journal of the American College of Cardiology, Vol. 43, No. 6, 2004. AF occurs in, for example, as many as 50% of patients undergoing cardiac operations. Patients with chronic AF have symptomatic tachycardia or low cardiac output and have a 5-10% risk of thromboembolic complications and events.

Many treatments for AF are performed directly on the heart itself. A common treatment for AF is cardioversion, alone or in combination with anti-arrhythmic therapy, to restore sinus rhythm. Recurrence rates after such therapy as high as 75% have been reported. Pharmacologic therapy is associated with adverse effects in a significant proportion of patients with AF. Other more current conventional methods of treating AF center around ablation (destruction) of the aberrant conduction pathways, either through a surgical approach or by use of various forms of energy to ablate conduction to electrically isolate discrete atrial regions. However, ablation causes structural damage to the heart. Unfortunately, these techniques involve actions performed directly on the heart itself, and further have significant adverse consequences.

Ablation can involve removal of ganglia of the autonomic nervous system. The pulmonary veins and atria have rich autonomic innervation, largely via autonomic ganglia that exist in fat pads in various well defined pericardial locations, some adjacent to the pulmonary veins. It has long been recognized that autonomic manipulation and intervention can dramatically alter the threshold for AF induction and persistence, and this knowledge has in the past been used experimentally to create appropriate models of AF. Emerging data from clinical trials based on strategies for PV isolation indicate that clinical success may be possible without achieving complete isolation. These observations indicate that what is being achieved is not only isolation of the triggers for AF, but also modification of the substrate by ablation of autonomic innervation. See, for example, Lazzara et al., Selective In Situ Parasympathetic Control of the Canine Sinoatrial and Atrioventricular Nodes, Circulation Research, Vol. 32, March 1973, p. 393-401; Scherlag et al., Stimulation of the Sino-Atrial Fat Pad Converts Focal Pulmonary Vein Firing Into Atrial Fibrillation in the Dog Heart, Circulation, Vol. 108, No. 17, Oct. 28, 2003, p. 396. Various researchers have reported that experimental interference with the autonomic ganglia in the fat pads can achieve modification of tendency to AF, and early clinical studies ablating around the mouths of pulmonary veins by targeting sites at which stimulation produces measurable changes in autonomic tone, indicating sites of autonomic innervation downstream from the autonomic ganglia, have shown success in abolishing AF. See, for example, Pappone et al., Pulmonary Vein Denervation Enhances Long-Term benefit After Circumferential Ablation for Paroxysmal Atrial Fibrillation, Circulation, Vol. 109, 2004, r7-r14.

Unfortunately, conventional surgical excision and conventional energy ablation have many problems. Responses to ablation energy delivery modalities include hyperthermia along with collagen shrinkage and other substantial scarring responses. Moreover, many ablation techniques suffer from control of energy delivery and extent of impact therefrom in tissues at or beyond the targeted location. For example, many RF energy ablation devices and techniques cause charring, which is associated with the high temperature gradient. Undesired energy dissipation into surrounding tissues is often observed using many conventional energy ablation techniques.

BRIEF SUMMARY OF THE INVENTION

Therefore, there is a need for improved treatment of cardiac arrhythmias that is not ablative.

The treatment of cardiac arrhythmias according to the present invention is a highly beneficial non-ablative technique for modifying neuronal signaling in tissue of the autonomic nervous system that innervates the heart through cardiac fat pads. This aspect provides benefit in providing the intended therapy without many of the other side effects and shortcomings of other conventional techniques, such as in particular conventional surgical excision and conventional energy ablation. In some embodiments, the invention advantageously provides temporary and reversible intervention of the intrinsic nervous system, rather than permanent alteration of various cardiac structures and, in some cases, of the nervous system.

The treatment of cardiac arrhythmias according to the present invention, which in some embodiments involves the application of non-ablative agent to the cardiac fat pads, is relatively easy to carry out, inasmuch as the major cardiac fat pads are readily identifiable and readily accessible. Moreover, the therapeutically effective amount of a non-ablative agent is less critical when the agent is applied to the cardiac fat pads than when it is applied to cardiac morphology.

One embodiment of the present invention is a kit for treating cardiac arrhythmia in a heart of a patient, comprising a nerve stimulator adapted for locating a target site on a cardiac fat pad in proximity to autonomic ganglia therein, the autonomic ganglia being a part of the autonomic nervous system; a source of non-ablative agent effective for modifying neuronal signaling by nerve tissue of the autonomic nervous system; and an agent delivery system. The agent delivery system comprises a proximal portion for coupling to the source; and a distal portion for delivering the agent from the source to the target site.

Another embodiment of the present invention is a kit for treating cardiac arrhythmia in a heart of a patient, comprising an electrode section adapted for being removably coupled to a stimulation generator for locating a target site on a cardiac fat pad in proximity to autonomic ganglia therein, the autonomic ganglia being a part of the autonomic nervous system; a source of non-ablative agent effective for modifying neuronal signaling by nerve tissue of the autonomic nervous system; and an agent delivery system. The agent delivery system comprises a proximal portion for coupling to the source; and a distal portion for delivering the agent from the source to the target site.

Another embodiment of the present invention is use of a non-ablative agent that is effective for modifying neuronal signaling by nerve tissue of the autonomic nervous system for the treatment of cardiac arrhythmia in a heart of a patient by stimulation of a cardiac fat pad to locate a target site on the cardiac fat pad in proximity to autonomic ganglia therein, the autonomic ganglia being a part of the autonomic nervous system, and by delivery of a therapeutically effective amount of the non-ablative agent to the target site.

Another embodiment of the present invention is a method of treating cardiac arrhythmia in a heart of a patient comprising preparing a source of non-ablative agent that is effective for modifying neuronal signaling by nerve tissue of the autonomic nervous system; stimulating a cardiac fat pad to locate a target site on the cardiac fat pad in proximity to autonomic ganglia therein, the autonomic ganglia being a part of the autonomic nervous system; and delivering a therapeutically effective amount of the non-ablative agent from the source to the target site.

Another embodiment of the present invention is use of a polyethylene glycol agent for the treatment of cardiac arrhythmia in a heart of a patient by delivery of a therapeutically effective amount of the polyethylene glycol agent to a cardiac fat pad in proximity to autonomic ganglia therein.

Another embodiment of the present invention is a method of treating cardiac arrhythmia in a heart of a patient comprising preparing a source of polyethylene glycol agent that is effective for modifying neuronal signaling by nerve tissue of the autonomic nervous system; and delivering a therapeutically effective amount of the polyethylene glycol agent from the source to a cardiac fat pad in proximity to autonomic ganglia therein, the autonomic ganglia being a part of the autonomic nervous system.

BRIEF DESCRIPTION OF THE SEVERAL VIEWS OF THE DRAWINGS

FIG. 9 is a schematic view of an illustrative injection system for injecting a dual component non-ablative agent.

FIG. 10 is a schematic view of another illustrative injection system for injecting a dual component non-ablative agent.

FIG. 11 shows a needle having a body that is sectioned with a partition to form separate and distinct lumens.

FIG. 12 shows a needle having a body within which two separate and distinct lumens are formed.

FIG. 13 shows a needle having a body that surrounds a second inner body to form separate and distinct lumens.

FIG. 27 is a table showing the incidence of post-operative AF from a clinical perspective.

DETAILED DESCRIPTION OF THE INVENTION, INCLUDING THE BEST MODE

Figure 1:
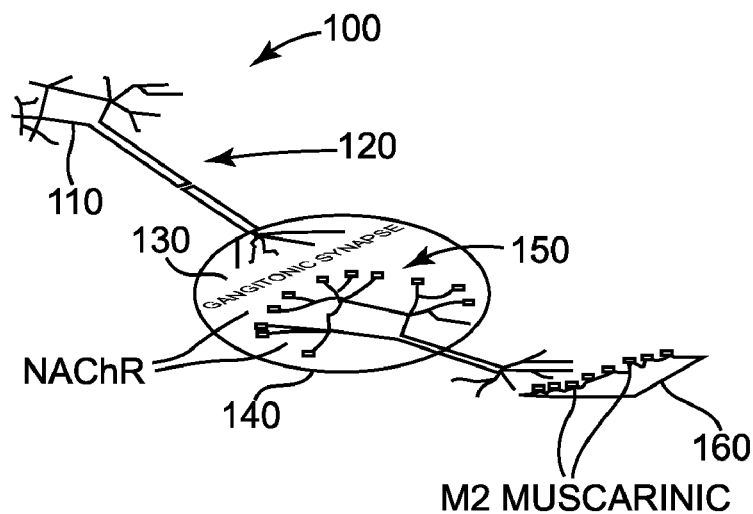
FIG. 1 is a schematic view of a nerve pathway from preganglionic neurons in the cervical vagus to the sinus node of a heart.

We have found that atrial fibrillation ("AF") may be treated by modifying neuronal signaling in ganglia of the peripheral autonomic nervous system contained in nerve tissue where the nerve tissue passes through epicardial fat pads of the heart. The ganglia of principal interest are in three epicardial fat pads: the right pulmonary ("RPV") fat pad, which supplies nerve fibers preferentially to the superior right atrium and sinus node; the inferior vena cava-left arterial ("IVC-LA") fat pad, which supplies nerve fibers to the AV node region and both atria; and a third fat pad ("SVC-AO") located between the superior vena cava and aorta. The SVC-AO fat pad provides efferent fibers to both the RPV and IVC-LA fat pads as well as additional fibers to both atria. These fat pads are of particular interest because they are accessible and distinctly identifiable, although other fat pads may be suitable as well. Of these three, the RPV fat pad and the IVC-LA fat pad are particularly preferred since efferent fibers from the SVC-AO fat pad are provided to them as well.

Neuronal signaling may be modified by the use of a non-ablative agent. While neuronal signaling enhancement may be desirable in some situations, neuronal signaling inhibition is particularly beneficial for treating cardiac arrhythmia, including atrial fibrillation. Suitable non-ablative agents include various polymers such as, for example, fibrin glue, alginate and polyethylene glycol ("PEG"), various cells such as, for example, fibroblasts (allogeneic or autologous), various neurotoxins such as, for example, Botulinum Type A, and various growth factors such as, for example, fibroblast growth factor. The non-ablative agent is introduced into the fat pads in any desired manner, including by injection from a catheter or by direct injection as in open chest surgery. Open chest surgical procedures for which modification of neuronal signal is beneficial include coronary artery bypass graft surgery and mitral valve surgery. The patient's heart may be beating throughout the injection.

The non-ablative agent may be, for example, fibrin glue formed from a one-to-one (1:1) ratio mixture of fibrinogen precursor to thrombin precursor. The ratio may be varied to achieve the desired characteristics; for example, the amount of fibrinogen relative to thrombin may be reduced to delay hardening. The fibrinogen and thrombin preferably are delivered separately to the targeted anatomical location in unmixed form via a dual channeled needles or separate needles, so that mixing occurs at the targeted anatomical location and not within the delivery system or outside of the targeted anatomical location. A satisfactory dose for a positive clinical result is a single 1 milliliter fibrin injection into the targeted anatomical location, although the dose may be varied as needed to achieve the desired therapeutic effect.

Generally where the non-ablative agent is or includes a biopolymer, the volume of the injectate may range from about 0.1 milliliters to about 5 milliliters, or from about 0.5 milliliters to about 2.0 milliliters.

The non-ablative agent may be, for example, fibroblast cells which are injected into a human patient's heart. The fibroblast cells may be injected in a solution of Bovine Serum Albumin ("BSA") or any other appropriate carrier solution that is biocompatible with human tissue. The volume of the injected solution may range in volumes from about 0.1 milliliters up to about 5 milliliters per injection, with as many as 10 million to 100 million fibroblast cells per injection. Multiple injections of fibroblasts may be delivered into the same anatomical location, either during the same medical treatment or over different medical treatments. For example, a "dose" of fibroblasts may be initially delivered to the treatment site with an appropriate "wait and see" designated period to assess clinical efficacy. Then, if deemed appropriate, additional fibroblasts may be injected into the same general anatomical location to augment the initial dosage to yield the desired clinical results. As many as 50 fibroblast injections or more may be injected into the same general anatomical location to yield the desired clinical results.

Other cell types may be used if they, like fibroblasts, are able to modify neuronal signaling. With further respect to cell delivery, they may be cultured from the patient's own cells (e.g. autologous), or may be foreign to the body such as from a regulated cell culture.

The non-ablative agent is delivered using an agent delivery system. In one particular and illustrative implementation of an agent delivery system, a cardiac arrhythmia is treated by delivering a non-ablative agent into one or more cardiac fat pads. A source of the non-ablative agent is provided. The agent delivery system is coupled to the source to deliver a volume of the non-ablative agent from the source to the desired location in the cardiac fat pad.

In another illustrative implementation of the agent delivery system, the material source is a preparation of a dual (or multiple) precursor non-ablative agent. A catheter is used to deliver the non-ablative agent to a fat pad containing autonomic ganglia that may be associated with the arrhythmia, to modify neuronal signaling at the autonomic ganglia for reducing or eliminating the arrhythmia. Separate syringes may be used for each of the precursors, and are connected to a branch section that in turn is connected to a multi-channeled catheter. Separate channels extend from each syringe through the branch section and to the end of the catheter. As the plungers of the syringes are depressed, the precursors are carried in their respective separate channels and mix in the fat pad in proximity to ganglionated plexuses immediately after clearing the catheter opening. The catheter is adapted to be injected into the fat pad with its end in proximity to the ganglionated plexuses.

An illustrative implementation of a method for assembling a cardiac arrhythmia treatment system, a delivery catheter is chosen that is capable of delivering a preparation of non-ablative agent into a fat pad containing autonomic ganglia. The delivery catheter is coupled to a source of the non-ablative agent.

In a variation of the method of assembly, an injector is included in the delivery catheter for injecting the non-ablative agent to the desired fat pad site via the delivery catheter.

Another illustrative implementation of a system for treating cardiac arrhythmia in a patient includes an agent delivery system and a source of non-ablative agent coupled to the agent delivery system. The agent delivery system is adapted to deliver the non-ablative agent from the source and substantially to a fat pad associated with the patient's heart. The agent delivery system may be either epicardial or endocardial, and the non-ablative agent may be delivered directly by the delivery system as during an open chest surgical procedure, or may be delivered with a percutaneous translumenal (preferably transvenous) delivery approach. Delivery may be transvascularly, for example, via the coronary sinus or the septal perforators, according to further appropriate device and method variations, respectively. Delivery may be by a transthoracic minimally invasive technique.

In one variation of this system, the agent delivery system further includes a contact member that is adapted to substantially contact the fat pads in proximity to autonomic ganglia therein, and the agent delivery system delivers the non-ablative agent to the contact member when it is substantially contacting the fat pads.

In another variation of this system, the agent delivery system includes a plurality of needles cooperating with the contact member. The plurality of needles are position by the agent delivery system into and substantially throughout the fat pads, so as to inject the fibroblast cells substantially into and throughout the fat pads for modifying neuronal signaling.

It is to be appreciated that various further aspects and modes are contemplated using the non-ablative agents according to the various cellular therapy aspects described herein. These further aspects and modes will be apparent to one of ordinary skill in the art, upon studying this patent document.

Various materials are useful as the non-ablative agent. One such material is a composition that comprises a scaffold from fibrin glue or other biopolymer agent combined with fibroblasts and/or neurotoxin and/or growth factor. Optionally the composition comprises only (1) a scaffold from fibrin glue or other biopolymer agent, (2) fibroblasts, (3) neurotoxin, (4) growth factor, or (5) any other biologic agent that blocks or impairs signal transmission in the autonomic ganglia contained in the fat pad.

In one implementation, the non-ablative agent includes autologous fibroblasts. Fibroblasts are nonconductive type of cell, and also secrete collagen, which acts as an electrical insulator. The autologous fibroblasts are derived from a biopsy of a patient's skin, amplified, and injected and/or grafted. In another implementation, such fibroblasts are removed from the patient and prepared in a manner so that they are suitable for delivery to the desired region of the heart. The preparation is coupled to an appropriate delivery catheter.

The treatment of cardiac arrhythmias according to the principles described herein is relatively easy to carry out, inasmuch as the major cardiac fat pads are readily identifiable and the ganglionated plexuses therein are readily accessible. Moreover, the therapeutically effective amount of a non-ablative agent is less critical when the agent is applied to the fat pads than when it is applied to cardiac morphology. The general non-criticality of the therapeutically effective amount is because non-ablative agent distributed in regions of the fat pad away from the autonomic ganglia have little or no effect on cardiac function.

Principles of Neuronal Signaling Modification in Autonomic Ganglia Contained in the Cardiac Fat Pads Mammalian hearts are innervated by both divisions of the autonomic nervous system. The parasympathetic nerve to the heart primarily supplies the atrium, especially the SA and AV nodes. Parasympathetic innervation of the ventricles is sparse. The sympathetic nerve to the heart also supplies the atria, including the SA and AV nodes, and richly innervate the ventricles as well. Both parasympathetic and sympathetic nerves pass through epicardial fat, where various collections of autonomic ganglia also known as ganglionated plexuses may be found. The autonomic ganglia contain many intrinsic neurons, most of which are multipolar, although some unipolar and bipolar neurons are also present. In the human heart, intrinsic autonomic ganglia and their associated nerves are found primarily embedded in epicardial fat, in which they form five atrial and five ventricular ganglionated plexuses. As disclosed in Armour, J. Andrew, et al., Gross and Microscopic Anatomy of the Human Intrinsic Cardiac Nervous System, The Anatomical Record, Vol. 247, 1997, pp. 289-298, atrial ganglionated plexuses ("AGP") may be found on the superior surface of the right atrium (the superior right AGP), the superior surface of the left atrium (the superior left AGP), the posterior surface of the right atrium (the posterior right AGP), the posterior medial surface of the left atrium (the posteromedial left AGP) (the posterior right AGP and the posteromedial left AGP fuse medially where they extend anteriorly into the interatrial septum), and the inferior and lateral aspect of the posterior left atrium (the posterolateral left AGP); while ventricular ganglionated plexuses ("VGP") may be found in fat surrounding the aortic root (the aortic root VGP, with right, anterior, left and posterior components), at the origins of the right and left coronary arteries, the latter extending to the origins of the left anterior descending and circumflex coronary arteries (the anterior descending VGP), at the origin of the posterior descending coronary artery (the posterior descending VGP), adjacent to the origin of the right acute marginal coronary artery (the right acute marginal VGP), and at the origin of the left obtuse marginal coronary artery (the obtuse marginal VGP). Neurons may also be located outside these sites, primarily in fat associated with branch points of other large coronary arteries.

While autonomic ganglia contained in many of the fat pads may receive treatment in accordance with the principles described herein, three epicardial fat pads are of principal interest. They are the right pulmonary ("RPV") fat pad which supplies nerve fibers preferentially to the superior right atrium and the sinus node, the inferior vena cava-left arterial ("IVC-LA") fat pad which supplies nerve fibers to the AV node region and both atria, and the superior vena cava-aorta ("SVC-AO") fat pad which supplies efferent fibers to both the RPV and IVC-LA fat pads as well as additional fibers to both atria.

Within the ganglionated plexuses, impulses are transmitted from one neuron to another at sites of functional apposition between neurons known as synapses. Although a few synapses in the central nervous system are electrical synapses, synaptic transmission is usually by a chemical neurotransmitter released by the axon terminal of the excited or presynaptic cell. The neurotransmitter diffuses across the synaptic cleft to bind with receptors on the postsynaptic cell membrane, which effects electrical changes in the postsynaptic cell.

One type of non-ablative agent is an injectable biopolymer of which fibrin glue and alginate are examples. Upon injection, the biopolymer becomes a semi-rigid scaffold about the autonomic ganglia which primarily mechanically disrupts neuronal signaling. The most likely mechanisms for the intended therapeutic response are that the biopolymer functions as a mechanical barrier and that the volume of the biopolymer produces a pressure sufficient to suppress neuronal signaling. Where the biopolymer itself is electrically insulating, it would be expected to inhibit conduction in any electrical synapses that may be present.

A typical fibrin matrix has an interesting property that makes it particularly advantageous for the control of AF in patients recovering from coronary artery bypass graft ("CABG") surgery and other cardiac surgery and procedures. As observed in Steinberg, Jonathan S., Editorial Comment: Postoperative Atrial Fibrillation, A Billion Dollar Problem, Journal of the American College of Cardiology, Vol. 43, No. 6, Mar. 17, 2004, pp. 1001-1003, AF is the most common complication associated with coronary artery bypass graft ("CABG") surgery. AF clusters tightly in the first two to four days after surgery. The clustering is in part the result of preexisting electrophysiologic vulnerability in the atria, but a number of contributing factors are likely to be present, along with preoperative electrical and structural abnormality as well as postoperative profibrillatory factors. As reported by Cummings, Jennifer E., Preservation of the Anterior Fat Pad Paradoxically Decreases the Incidence of Postoperative Atrial Fibrillation in Humans, Journal of the America College of Cardiology, Vol. 43, 2004, pp. 994-1000, the common practice of removing the anterior fat pad during CABG appears to be proarrhythmic, and may be due to upset of the balance of sympathetic and parasympathetic regulation. Steinberg alternatively proposes that the heterogeneous loss of atrial innervation due to removal of the anterior fat pad may aggravate heterogeneity of refractoriness, which is important in promoting reentry as the mechanism of AF and is a critical determinant of AF. If so, a number of issues are suggested. One such issue is whether complete denervation might be more effective than preserved innervation. Another such issue is whether there are important detrimental effects on sinus node or AV node function, or other autonomic cardiac responses, when the fat pads are removed.

The interesting property that makes a typical fibrin matrix particularly advantageous for the control of AF in patients recovering from coronary artery bypass graft ("CABG") surgery and other cardiac surgery and procedures is that the typical fibrin matrix is maintained for from only seven to ten days, at which time it begins to degrade. The neuronal signaling modification for the typical fibrin matrix therefore is temporary, and may be used to achieve significant modification effectively similar to complete denervation during a critical period following the surgery or procedure, followed by a restoration of function to avoid any detrimental effects that may have otherwise resulted from complete irreversible denervation. Even if the SVC-AO fat pad were removed, the remaining RPV fat pad and the IVC-LA fat pad may be treated with a biopolymer to achieve significant modification of neuronal signaling effectively similar to complete denervation during the critical period following the surgery or procedure, followed by a restoration of function in the remaining RPV fat pad and the IVC-LA fat pad.

FIG. 1 is a simplified schematic representation showing a nerve pathway 100 from pre-ganglionic neurons 110 in the cervical vagus 120 to sinus node 160. The pre-ganglionic neurons 110 communicate with post-ganglionic neurons 150 via the ganglionic synopses 130 within the RPV or sinus node fat pad 140. The post-ganglionic neurons 150 are coupled to the sinus node 160.

Figure 2:
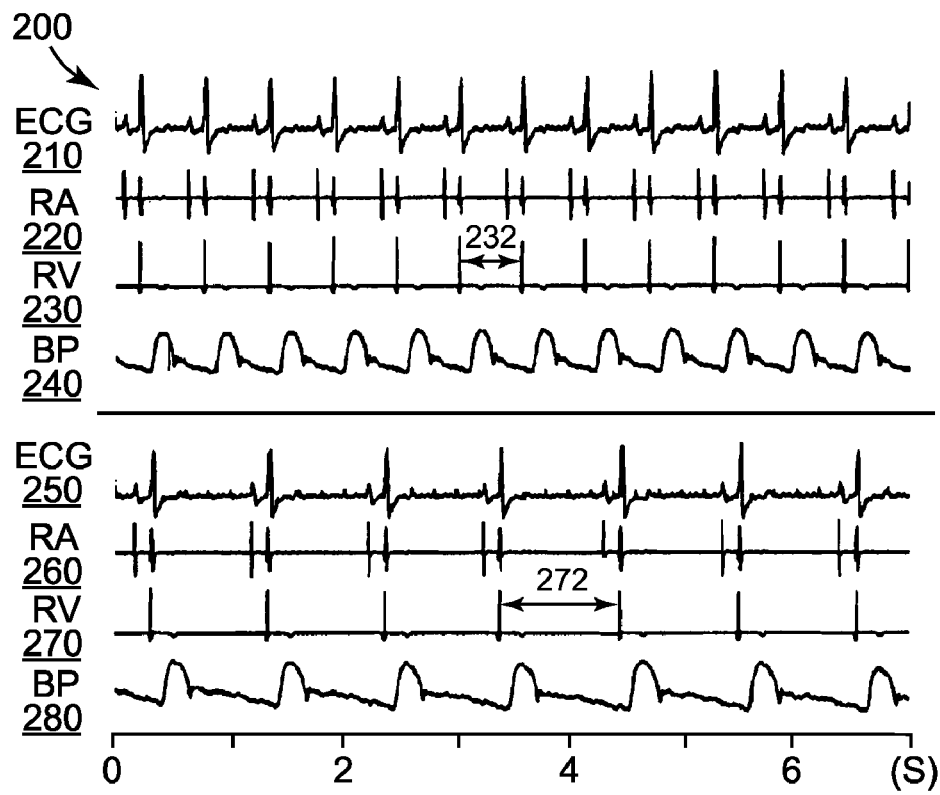
FIG. 2 is a graph showing in the time domain the results after a period of time of injecting fibrin glue into the sinus node fat pad of a canine test subject.

FIG. 2 is a graph 200 showing in the time domain the results after a period of time of injecting fibrin glue into the sinus node fat pad 140 (FIG. 1) of a canine test subject. Time domain traces 210, 220, 230, and 240 represent control data for the sinus rhythm response, and show respectively the ECG, right atrium RA, right ventricle RV, and blood pressure BP signals approximately 4 weeks after injecting the fibrin mixture but prior to applying an electrical stimulus to the cervical vagus 120. Time domain traces 250-280 show the same physiologic responses after an electrical stimulation has been applied to the cervical vagus 120. Taken together, traces 250-280 indicate a significant "slowing down" of the animal's heart rate by the increased time interval between cardiac events. We believe that the fibrin glue matrix reabsorbs so that the electrical stimulation of the cervical vagus 120 has become effective and is able to initiate a parasympathetic response to slow down the animals heart rate.

Another type of non-ablative agent is an injectable preparation of fibroblast cells. A fibroblast is a connective tissue cell form the fibrous tissues in the body. We believe that when injected into a fat pad in proximity to a ganglionated plexuses, the fibroblasts engraft in the vicinity of the synapses and mechanically disrupt neuronal signaling in the autonomic ganglia. Fibroblasts are electrically insulating and would be expected to inhibit transmission in any electrical synapses that may be present. The effect is persistent.

Another type of non-ablative agent is an injectable preparation of fibroblast growth factor ("FGF"). Fibroblast growth factor describes family of cytokines that act on the fibroblasts within the body to induce fibroblast proliferation. Most cells with various organs of the body, including the nervous system and the heart, possess receptors for FGF and therefore are susceptible to its biological effect. Additionally, fibroblast growth factor can be bound to various biopolymers to form a conjugated molecule. Suitable biopolymers include polysaccharides and muco-adhesives. FGF is a small protein that can be easily denatured when exposed to heat or acid. When the FGF is conjugated, the protein is more stable. Conjugation can further program the FGF's release from its carrier in order to ensure that the desired action of the GF, on a specific site, is maintained.

Another type of non-ablative agent is an injectable preparation of a neurotoxin. Useful neurotoxins include botulinum toxins such as Botulinum Type A, which is available from Allergan Inc. of Irvine, Calif. under the name BOTOX® Purified Neurotoxin Complex. Another botulinum toxin well known in the art is Botulinum Type B. We believe that when injected into a fat pad in proximity to a ganglionated plexuses, the botulinum toxin disrupts neuronal signaling in the autonomic ganglia. The effect is temporary, and the neurons generally recover in about three to six months.

Preparation Techniques for Some Non-Ablative Agents

Fibroblasts may be used to modify neuronal signaling in autonomic ganglia contained in the cardiac fat pads. Fibroblasts are normally associated with healing of tissue. Upon activation, a transition of cell types to activated phenotypes occurs. The activated phenotypes having a fundamentally different biologic function from corresponding quiescent cells in normal tissue. These cellular phenotypes (arising from coordinated gene expression) are regulated by cytokines, growth factors, and downstream nuclear targets. They can survive and multiply even in low oxygen environments. Quiescent fibroblasts in normal tissue primarily are responsible for steady-state turnover of the extracellular matrix.

Fibroblast transplantation is used to deliver fibroblast cells to ganglionated plexuses in the fat pads. The nature of fibroblasts is to fill in space within tissue. When injected into the fat pads, fibroblasts fill in space within the fat pads, but are genetically programmed to cease proliferation and multiplication once they begin to crowd. In one particular beneficial regard, fibroblasts do not undergo a transition stage from proliferating to mature cells as do skeletal myoblasts when they transform to myotubes. Fibroblasts therefore have a more homogeneous excitation pattern as compared to skeletal muscle. Moreover, the electrophysiological properties of fibroblasts are fairly consistent from one fibroblast to the next.

An illustrative method of fibroblast preparation is to use autologous fibroblasts from the patient's own body, such as fibroblasts from dermal samples, and subsequently appropriately prepare them (e.g. in a culture/preparation kit) and transplant them to the desired location.

Skin fibroblasts potentiate the migration to PDGF and increase collagen accumulation and MMP synthesis, and net collagen accumulation. This formation of collagen matrix coupled with the lack of gap junction proteins in fibroblasts, creates the potential for electromechanical isolation in nerve tissue.

Fibroblasts can be biopsied from many tissues in the body (lungs, heart, skin) isolated, amplified in culture, and introduced via injection, graft delivery, grafting, and so forth, either with or without a polymeric carrier or backbone, into the desired location. Preparations of fibroblasts may include primarily or only one material or combinations of materials. For example, a preparation that include fibroblast cells may also include other materials, such as fluids or other substrates to provide the cells in an overall preparation as a cellular media that is adapted to be injected, such as in particular through a delivery lumen of a delivery catheter. In one particular example, the fibroblast cells may be combined with a biopolymer material such as fibrin glue, which may itself be provided as two precursor materials that are mixed to form fibrin glue that assists in neuronal signaling modification when delivered with cells at the desired location within the heart. Collagen or preparations thereof, including precursors or analogs or derivatives of collagen, is also considered useful in such combination.

Generally, a polymer is considered to be a chain of multiple units or "mers." A polymer tolerated by the body may be delivered in the vicinity of ganglionated plexuses in the cardiac fat pads, where it primarily mechanically disrupts neuronal signaling. The most likely mechanisms for the intended therapeutic response are that the polymer functions as a mechanical barrier and that the volume of the polymer produces a pressure sufficient to suppress neuronal signaling. For post-operative treatment, a suitable polymer is injectable, illustratively via a standard 23 guage needle. It has a suitable viscosity characteristic or a suitably rapid gelling or solidification characteristic so that it remains generally at the intended location. Its viscosity at time of injection should be acceptable for injection, illustratively less than about 7.5 psi force required on a syringe. Its residence time and stiffness properties should be suitable to maintain suppression of neuronal signaling in the autonomic ganglia for a minimum of about five days, and should experience resorption or dissolution in less than about thirty days without significant metabolic byproducts. Illustratively, it should have a Compressive Modulus (Young's) of between about twelve and forty kPa. Its pH should be physiologic, and it should be sterile. A variety of polymers are suitable. Suitable fibrin sealants are available from a variety of manufacturers, such as Crosseal® and Quixil® fibrin sealant available from Omrix Pharmaceuticals of New York, N.Y., and HemaSeel Fibrin Sealant available from Haemacure Corporation of Sarosota, Fla. A suitable fibrin glue may also be made from cryoprecipitate, which is a source of autologous fibrinogen prepared from a subject's own plasma. Other suitable polymers include synthetic resorbable self-curing hydrogel materials. One such material is DuraSeal® sealant, which is available from Confluent Surgical of Waltham, Mass. The DuraSeal sealant is a polyethylene glycol based sealant. Another such material is CoSeal® surgical sealant, which is available from Angiotech Pharmaceuticals of Vancouver, British Columbia, Canada, and Baxter Healthcare Corporation of Fremont, Calif. The CoSeal surgical sealant is made of two synthetic polyethylene glycols or PEGs, a dilute hydrogen chloride solution, and a sodium phosphate/sodium carbonate solution. At the time of administration, the mixed PEGs and solutions form a hydrogel that adheres to tissue. Both the DuraSeal and CoSeal sealants polymerize within seconds and are broken down in the body within weeks due to hydrolysis. Other suitable polymers include cyanoacrylate glues. Other suitable polymers include polyethylene oxide ("PEO"), PEO-poly-l-lactic acid ("PLLA-PEO block copolymer"), poly(N-isopropylacrylamide-co-acrylic acid) ("poly(NIPAAm-co-Aac)"), a pluronic agent, and poly-(N-vinyl-2-pyrrolidone) ("PVP"). Other suitable polymers include sugars such as monosaccharides, disaccharides, and trisaccharides. A class of materials generally known as alginates are suitable polymers. Other suitable polymer include various beads and hydrogels which may be injected alone to mechanically disrupt neuronal signaling, or with other material to administer therapeutics along with mechanical disruption. The polymer-based beads and hydrogels may contain only polymer material, or may include cells such as stem cells, fibroblasts, or skeletal cells; proteins, plasmids, or genes; growth factors in either protein or plasmid form; chemo-attractants; fibrin factor (or fragment) E; RDG binding sites; various pharmaceutical compositions; neo-tissues; or other therapeutically beneficial materials; or any combination of the foregoing. Suitable polymers for beads and hydrogels include fibrin glue, collagen, alginates, and chitosan. Other suitable polymers include hyaluronic acid, sodium hyaluronate, and other formulations, Restylane Injectable Gel available from Q-Med of Scandinavia or from Medicis Aesthetics Holdings Inc., and Synvisc hyaluronic acid available from Gensyme. The polymer materials described herein generally illustrate certain broader classes of materials, which classes may contribute additional alternatives as would be apparent to one of ordinary skill. Where a compound is herein identified in relation to one or more embodiments described herein, precursors or analogs or derivatives thereof are further contemplated. For example, material structures that are metabolized or otherwise altered within the body to form such compound are contemplated. Or, combination materials that react to form such compound are also contemplated. Additional materials that are also contemplated are those which have molecular structures that vary insubstantial to that of such designated compounds, or otherwise have bioactivity substantially similar thereto with respect to the intended uses contemplated herein (e.g. removing or altering non-functional groups with respect to such bioactive function). Such group of compounds, and such precursors or analogs or derivatives thereof, is herein referred to as a "compound agent." Similarly, reference herein to other forms of "agents", such as for example "polymer agent" or "fibrin glue agent" may further include the actual final product, e.g. polymer or fibrin glue, respectively, or one or more respective precursor materials delivered together or in a coordinated manner to form the resulting material.

An illustrative biopolymer, fibrin glue, contains polymerized fibrin monomers, and is further herein considered an illustrative example of a biopolymer since its components are biological. Thrombin in a kit is an initiator or catalyst which enzymatically cleaves fibrinogen into fibrin. The monomers can then polymerize into a fibrin gel or glue. A useful fibrin glue is TISSEAL™, which is available from Baxter Healthcare, Inc. of Chicago, Ill. Other examples of fibrin glues are disclosed in Sierra, DH, "Fibrin sealant adhesive systems: a review of their chemistry, material properties and clinical applications," J. Biomater Appl., Vol. 7, 1993, pp. 309-52, which hereby is incorporated herein in its entirety by reference thereto.

The biopolymer may be used alone or in combination with another material. In one beneficial combination, a preparation of fibroblast cells and a biopolymer is delivered into fat pads to modify neuronal signaling in autonomic ganglia contained in the cardiac fat pads. The biopolymer enhances retention of the fibroblast cells at the location where they are delivered, and both may contribute to modification of neuronal signaling. One particular example of a material that provides significant benefit in such combination with fibroblast cellular therapy is fibrin glue.

Fibroblast growth factor describes family of cytokines that act on the fibroblasts within the body to induce fibroblast proliferation. There are perhaps twenty-three members of the FGF superfamily, which interact with at least four distinct types of cell-surface receptors. Fibroblast growth factors are described in further detail in various material from R&D Systems Inc. of Minneapolis, Minn., including R&D Systems Inc. 2001 Catalog: Fibroblast Growth Factors, 2001 (http://www.rndsystems.com/asp/g_SiteBuilderasp?BodyID=308); and R&D Systems Inc. 1996 Catalog: Fibroblast Growth Factor 9, 1996 (http://www.rndsystems.com/asp/g_sitebuilderasp?bBodyOnly=1&bodyId=199); see also Gospodarowicz, Denis, Fibroblast growth factor: chemical structure and biologic function, Clinical Orthopedics and Related Research, Number 257, August 1990, pp. 231-248.

Neurotoxin may be used to modify neuronal signaling in autonomic ganglia contained in the cardiac fat pads. An example of a useful neurotoxin is botulin, which is any of several potent neurotoxins produced by botulinum and resistant to proteolytic digestion. The mechanism of action of the Botulinum Toxin Type A is disclosed in product information published by Allergan Inc., Botox: mechanism of action (http://www.botox.com/site/professionals/product_info/mechanism_of_action.asp), printed 2004. Essentially, Botulinum toxin type A blocks acetylcholine release by cleaving SNAP-25, a cytoplasmic protein that is located on the cell membrane and that is required for the release of this transmitter.

Various materials described herein are particularly effective and beneficial, such as, for example, fibrin glue and related agents, analogs and derivatives thereof. However, other suitable materials may be used in certain applications, either in combination or as substitutes for such particular materials mentioned. In one particular regard, where fibrin glue or related biopolymer agents are herein described, it is further contemplated that collagen or precursors or analogs or derivatives thereof, may also be used in such circumstances, in particular in relation to modifying neuronal signaling in autonomic ganglia. Moreover, where collagen is thus included, precursor or analogs or derivatives thereof are further contemplated, such as, for example, structures that are metabolized or otherwise altered within the body to form collagen, or combination materials that reach to form collagen, or material whose molecular structure varies insubstantially to that of collagen such that its activity is substantially similar thereto with respect to the intended uses contemplated herein (e.g., removing or altering non-functional groups with respect to such function). Such a group of collagen and such precursors or analogs or derivatives thereof may be referred to as a "collagen agent." Similarly, other "agents" such as, for example, biopolymer agent, fibrin glue agent, neurotoxin agent, and growth factor agent may further include the actual final product, their precursors separately, or their precursors delivered together or in a coordinated manner to form the resulting material.

While modification of neuronal signaling is achieved with a non-ablative agent, it will be appreciated that terms such as "non-ablative" as well as terms such as "without substantially ablating," "substantially non-ablative," "minimally-ablative," and others of similar import are intended to mean that the primary mechanism of action is not ablation of tissue, and that the majority of tissue is not ablated at the location of material delivery. However, it is also to be considered that any material being delivered into a tissue may result in some attributable cell death. For example, the pressure of injection, or even the needle penetration itself, may be responsible for killing some cells, but such is not the mechanism by which modification of neuronal signaling is primarily achieved. In a similar regard, at some level it may be the case that all materials have some toxicity to all cells. Therefore, a material is herein considered non-ablative with respect to neurons if such material does not substantially ablate neural tissue as delivered, and neural tissue can generally survive in the presence of such material in such delivered quantities.

It is also contemplated that cell delivery according to the invention may result in certain circumstances in substantial cell death in, or subsequent apoptosis of, the original cells in the region of tissue where delivery is performed, but such original cells are replaced by transplanted cells. The result of such circumstance remains beneficial, as the structure remains cellular as a tissue and is considered preferable over a scarred and damaged area as would result from classic ablation techniques.

In addition, despite the significant benefit provided according to the various aspects of the invention for non-ablative modification of neuronal signaling, further embodiments may also include ablative modes, such as for example by combining cell or fibrin glue delivery with ablation, either concurrently or serially.

Methods of Delivering Non-ablative Agent to the Fat Pads

A variety of methods may be adapted to deliver non-ablative agents to the autonomic ganglia contained in the fat pads. Suitable methods are described in U.S. patent application Ser. No. 10/329,295 filed Dec. 23, 2002 (Randall J. Lee and Mark Maciejewski, System and Method for Forming a Non-Ablative Cardiac Condition Block), International Publication No. WO 03/094855 A1 published Nov. 20, 2003 (Randall J. Lee and Mark Maciejewski, System and Method for Treating Cardiac Arrhythmias with Fibroblast Cells); U.S. patent application Ser. No. 10/349,323 filed Jan. 21, 2003 (Randall J. Lee, System and Method for Forming a Non-Ablative Cardiac Conduction Block), and International Publication No. WO 03/095016 A1 published Nov. 20, 2003, all of which are hereby incorporated herein in their entirety by reference thereto.

Figure 3:
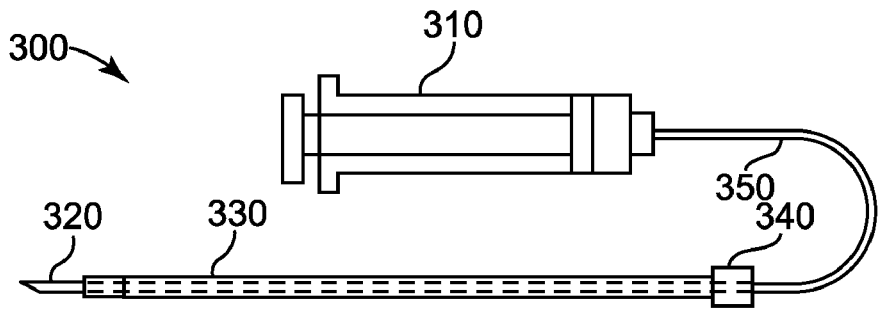
FIG. 3 is a schematic view of a catheter injection system for a single component non-ablative agent.

FIG. 3 is a schematic view of an illustrative catheter injection system 300 for a single component non-ablative agent. The catheter injection system includes a delivery catheter 330, which is an elongated body that connects at its proximal end by coupler 340 to a tube 350 from the syringe 310, and has a needle 320 at its distal end. A lumen extends through the delivery catheter 330. The needle 320 extends beyond the distal tip of the delivery catheter 330 and into tissue for delivering agent from the syringe 310 into the tissue. The needle 320 may be fixed relative to delivery catheter 330, or may be axially moveable. The needle 320 may take any of a variety of different forms, including the straight sharp-tip type, and the hollow screw-shaped type to aid in anchoring at the target site.

Figure 4:
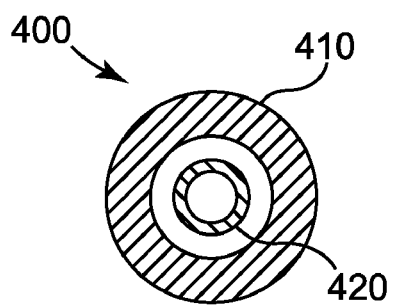
FIG. 4 is a transverse cross sectional view of a catheter in which a needle is slideably housed in a single lumen shaft within the catheter body.
Figure 5:
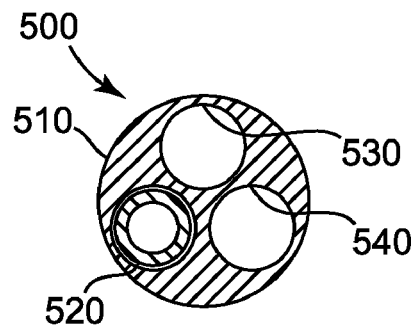
FIG. 5 is a transverse cross sectional view of a catheter that has three lumens, one of which slideably houses a needle.
Figure 6:
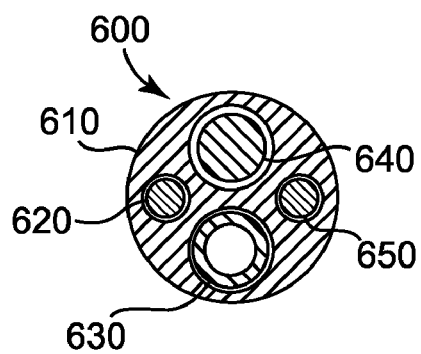
FIG. 6 is a transverse cross sectional view of a catheter that has four lumens, which slideably house a needle, a pull-wire, and two lead wires.

The nature of the delivery catheter 330 may vary considerably depending on the procedure being carried out. FIG. 4 is a transverse cross sectional view of a catheter 400 in which a needle 420 is slideably housed in a single lumen shaft within a catheter body 410. FIG. 5 is a transverse cross sectional view of a catheter 500 in which a needle 520 is slideably housed in a lumen within a catheter body 510. Additional lumens 530 and 540 are provided in the catheter body 510 and may have various different functions, depending upon the particular needs. FIG. 6 is a transverse cross sectional view of a catheter 600 that has four lumens. One of the lumen slideably houses a needle 630, one of the lumen slideably houses pull wire 640, and the remaining two lumens house lead wires 620 and 650, which may be connect to, for example, mapping electrodes. The mapping electrodes are part of a mapping system for stimulating and detecting an appropriate site for material injection, including for injection into the fat pads from within the heart (endocardial).

It will be appreciated that the catheter system 300 of FIG. 3 and the catheter variations shown in FIGS. 4-6 are merely illustrative. Various different types of catheter systems and catheters may be used to deliver and inject non-ablative agent into the fat pads.

Figure 7:
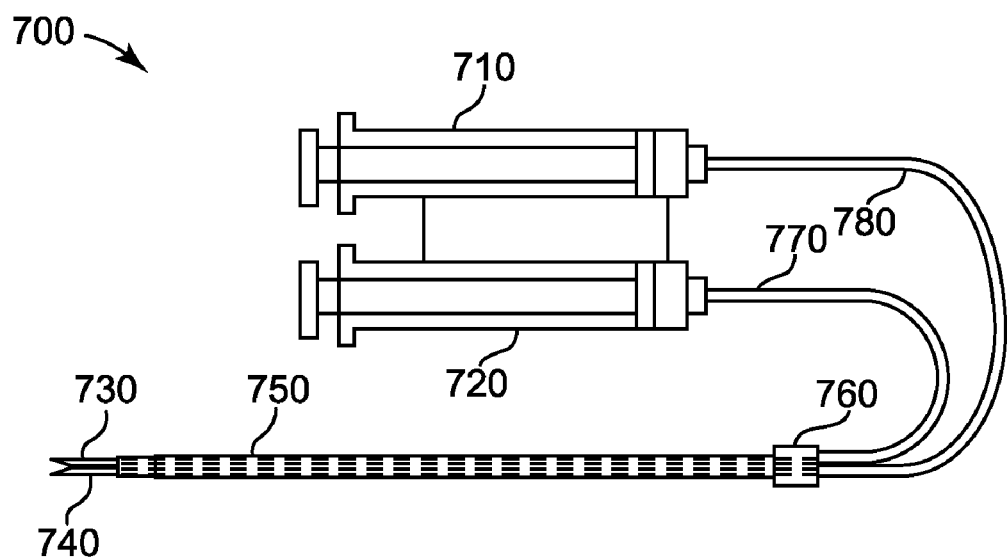
FIG. 7 is a schematic view of an illustrative catheter injection system for a dual component non-ablative agent.

FIG. 7 is a schematic view of an illustrative catheter injection system 700 for a dual component non-ablative agent. The catheter injection system includes a delivery catheter 750, which is an elongated body that connects at its proximal end by coupler 760 to two tubes 770 and 780 from respective syringes 720 and 710, and has respective needles 730 and 740 at its distal end. The needles 730 and 740 extend beyond the distal tip of the delivery catheter 750 and into tissue for delivering agent from the syringes 710 and 720 into the tissue. The needles 730 and 740 may be fixed relative to delivery catheter 750, or may be axially moveable.

The catheter injection system 700 is particularly suitable for use with dual component non-ablative agents for which the components are biopolymer precursors, such as, for example, fibrin glue. When fibrinogen is mixed with thrombin in the presence of calcium ions, it forms fibrin, a filamentous protein that is essential for the clotting of blood. In certain applications, it is desirable to mix fibrinogen and thrombin in a specific region of body tissue, such as the fat pads around the heart (epicardial) or in the heart (endocardial). In general, for many of these applications, it is not desirable to allow the two components to mix other than precisely where they are to be injected. In the catheter injection system 700, the two components are kept entirely separate until the emerge from the distal ends of the needles 730 and 740, so that no opportunity is present for the components to polymerize in the catheter injection system 700 or in any other place than where injected.

Figure 8:
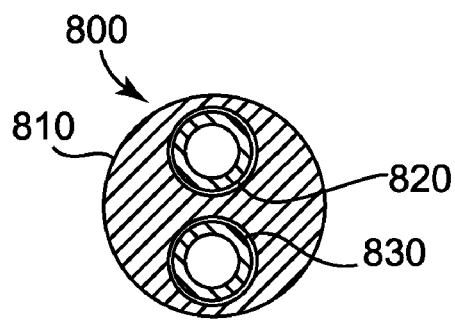
FIG. 8 is a transverse cross sectional view of a catheter that has two lumens which slideably house respective needles.

FIG. 8 is a transverse cross sectional view of a catheter 800 suitable for the catheter injection system 700. The catheter 800 has two lumens in catheter body 810 which slideably house respective needles 820 and 830. The needles 730 and 740 (FIG. 7) are in fluid communication with the syringes 720 and 710 through the lumens. The fibrin glue precursors flow from their respective syringes to their respective needles along entirely separate channels, so that the precursors mix only after injection into the tissue.

It will be appreciated that the catheter system 700 of FIG. 7 and the catheter variation shown in FIG. 8 are merely illustrative. Various different types of catheter systems and catheters may be used to deliver and inject non-ablative agent into the fat pads.

FIG. 9 is a schematic view of an illustrative injection system for injecting a dual component non-ablative agent during, for example, open chest surgery. The injection system of FIG. 9 includes two syringes 940 and 960, which may be molded as a single unit or which may be separate syringes held together by clamp 950. The syringes 940 and 960 are shown as having respective hollow barrels fitted with their respective plungers. Alternatively, the plungers from each barrel may be joined together, so that they may be depressed simultaneously. A needle section 900 has a dual channeled portion 910 and branch portions 920 and 930, which are respectively coupled to the syringes 940 and 960. The two components of the non-ablative agent from the syringes 940 and 960 are directed through the respective branches 920 and 930 into respective channels in the channeled portion 910. They are kept entirely separate until the emerge from the distal end of the needle section 900, so that no opportunity is present for the components to polymerize in the injector or in any place other than where injected.

FIG. 10 is a schematic view of another illustrative injection system for injecting a dual component non-ablative agent during, for example, open chest surgery. The injection system of FIG. 10 is identical to that of FIG. 9, except for differences in a needle section 1000. The needle section 1000 has a helical dual channeled portion 1010 and branch portions 1020 and 1030, which are respectively coupled to the syringes 940 and 960. The two components of the non-ablative agent from the syringes 940 and 960 are directed through the respective branches 1020 and 1030 into respective channels in the channeled portion 1010. They are kept entirely separate until the emerge from the distal end of the needle section 1000, so that no opportunity is present for the components to polymerize in the injector or in any place other than where injected.

The needle 900 (FIG. 9) is introduced into the tissue by linear motion, while the needle 1000 (FIG. 10) is introduced into the tissue with a twisting motion and is particularly suitable for moving tissue such as the heart. The needle 900 and the needle 1000 preferably are channeled all the way to their distil tips.

While the injection systems of FIGS. 9 and 10 are dual channeled, any number of separate channels may be provided in the needle. The separate channels of the multi-channeled needle guide the respective precursors to the distal tip of the needle. The tip is injected into a particular region of body tissue, such as the fat pads around the heart or into the heart. The dispensed materials leave the tip, then mix in the injected tissue rather than inside of the needle or the syringe. Any number of barrels may be present on the syringe with a corresponding number of channels extending from the barrels down to the distal tip. The multi-channeled needle may be removed from the barrels for separate disposal, or may be fixed to the hollow barrels. Moreover, the catheter injection systems 300 (FIG. 3) and 700 (FIG. 7) may be provided with multi-channeled needles instead of the single channeled needles shown.

FIGS. 11, 12 and 13 show just a few of the possible way in which dual channels may be provided in a needle. FIG. 11 shows a needle 1100 having a body 1110 that is sectioned with a partition 1140 to form separate and distinct lumens 1120 and 1130. FIG. 12 shows a needle 1200 having a body 1210 within which two separate and distinct lumens 1220 and 1230 are formed. FIG. 13 shows a needle 1300 having a body 1310 that surrounds a second inner body 1340 to form separate and distinct lumens 1320 and 1330. While the lumens and needles are shown as round, they may be oval or any other desired shape.

It will be appreciated that the catheter injection systems and injection systems described herein are illustrative, and other suitable substitutes may be used in order to achieve the objective of delivering two precursor materials and mixing them to form the injected agent. For example, some types of precursor materials may be mixed prior to delivery from the distal portions of the needle, such as at a mixing chamber in proximity to the coupler of the catheter, or prior to coupling to the delivery catheter. Moreover, more than one delivery device may be used for each of two materials being delivered; for example, two separate and distinct needles may be used to deliver each of two precursor materials from respective sources located outside of the patient's body.

EXPERIMENTAL EXAMPLE 1

Surgical preparation was as follows. Two adult mongrel dogs (body weight 23-30 kg) were premedicated with thiopental sodium (20 mg/kg) intravenously, and intubated and ventilated with room air supplemented with oxygen as needed to maintain normal arterial blood gases by a respirator (type Narkomed 2, available from North American Drager Inc. of Telford, Pa.). Anesthesia was then maintained with 1-2% isoflurane throughout the experiment. Normal saline solution was infused IV at 100-200 mL/h to replace spontaneous fluid loses. Standard surface ECG leads (I, II, III) were monitored continuously throughout the entire study. Intermittent arterial blood gas measurements were taken and ventilator adjustments were made to correct any metabolic abnormalities. Rectal temperature was monitored with a rectal probe and an electrical heating pad under the animal and operating-room lamps were used to maintain a body temperature of 360 C to 370 C.

The right femoral artery was cannulated and a micromanometer-tipped catheter pressure transducer (available from Millar, Inc. of Houston, Tex.) was inserted and advanced into the thoracic aorta near the aortic valve to monitor systemic blood pressure. After the chest was opened through a median sternotomy, a pericardium cradle was created to support the heart. Custom-made Ag—AgCl quadripolar plate electrodes were sutured to the high right atrium and right ventricular apex for bipolar pacing and recording. Similar bipolar plate electrodes were also used for stimulation of two epicardial fat pads through which parasympathetic neural pathways selectively innervating the sinus or sinoatrial ("SA") node and the atrioventricular ("AV") node, respectively. The SAN fat pad was located at the right pulmonary vein (RPV)-atrial junction. The AVN fat pad was located at the junction of inferior vena cava and the left atrium (IVC-LA). All signals (surface ECGs, right atrial and ventricular electrograms, arterial blood pressure) were amplified, filtered, digitized and continuously displayed on a monitoring system (Prucka Engineering, Inc.). In addition these signals along with calibration signals were simultaneously recorded on magnetic tape (Vetter Digital, 4000A) for later computer analysis with AxoScope (Axon Instruments) and custom software programs.

The study protocol was as follows. The study had 2 stages, initial acute surgery, and observation after 4 weeks recovery. During the initial acute surgery we tested the vagal effects by delivering fat pads' electrical stimulation. The latter was delivered as rectangular pulses at 20 Hz (50 ms interval), 0.2-0.5 ms duration, and amplitude of 3-5 mA. During the final study, in addition to the fat pads, we also delivered electrical stimulation to the cervical vagus (while intact, as well as after decentralization). In this case the parameters were 3, 5 and 10 Hz, 1 ms duration, and amplitude 5 mA.

Fibrin glue was injected during the initial acute study into the 2 fat pads. We used Quixil, a 2-component mixture of thrombin and BAC that was delivered through a 2-channel injector and 23 gauge needle, so that the 2 components mixed only inside the fat pads. The needle was inserted 1-2 mm under the epicardial surface of the fat pads. A total of 1 ml fibrin glue was delivered in each fat pad.

Figure 14:
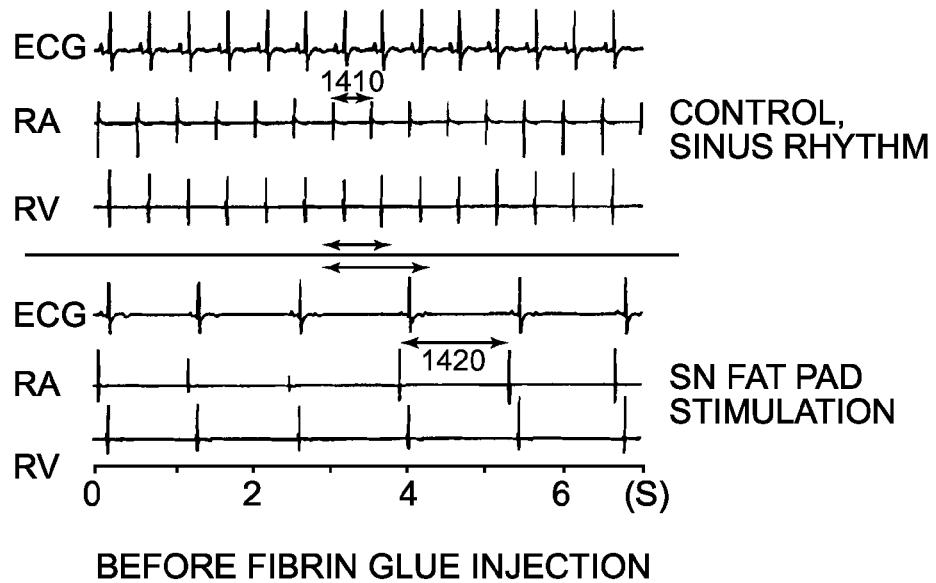
FIG. 14 is a graph showing in the time domain the impact on sinus rhythm of SN fat pad simulation before fibrin glue injection.
Figure 15:
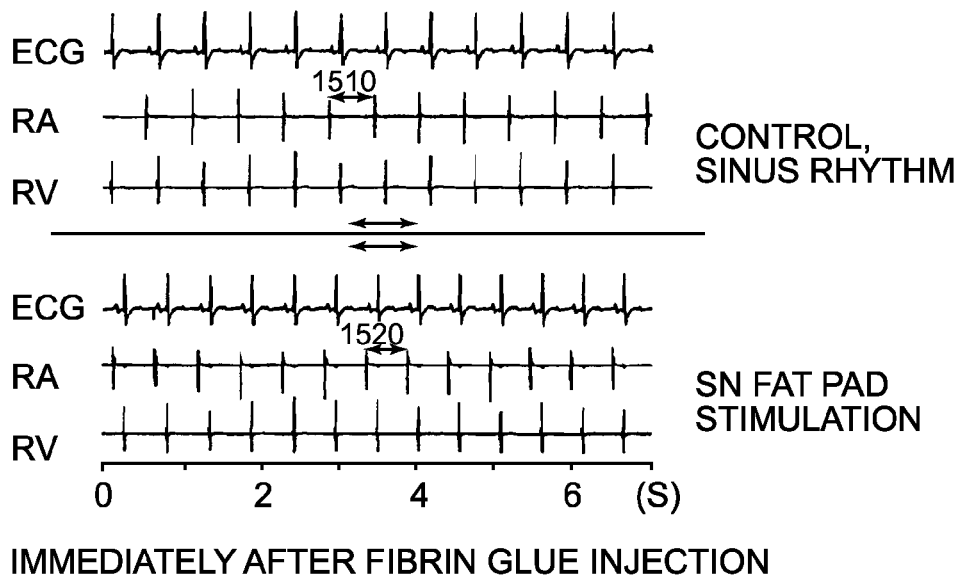
FIG. 15 is a graph showing in the time domain the impact on sinus rhythm of SN fat pad simulation immediately after fibrin glue injection.
Figure 16:
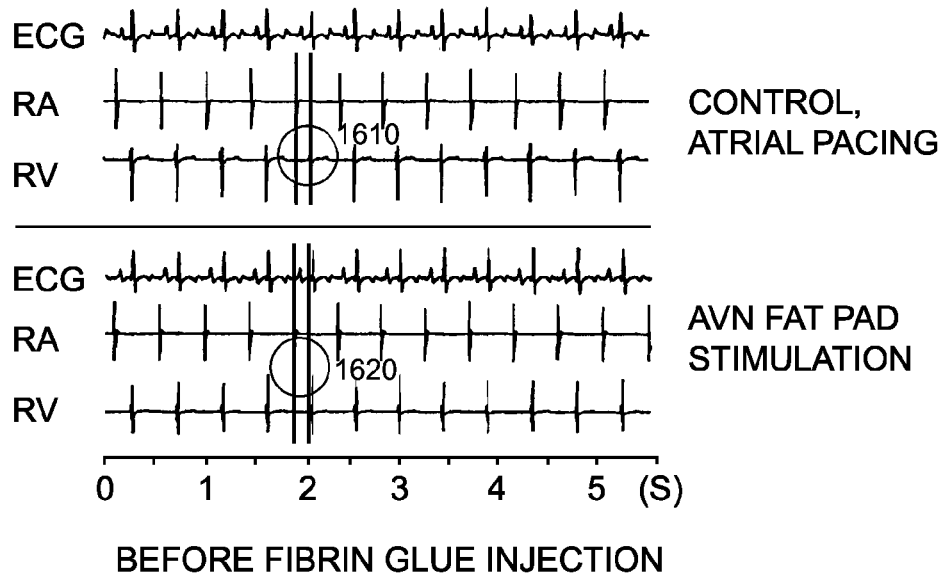
FIG. 16 is a graph showing in the time domain the impact on atrial pacing of AVN fat pad simulation before fibrin glue injection.
Figure 17:
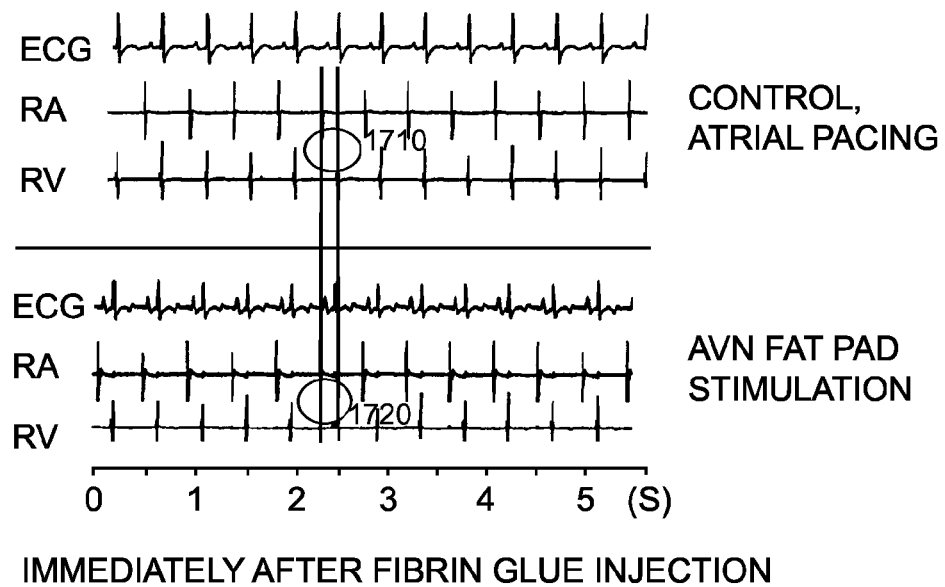
FIG. 17 is a graph showing in the time domain the impact on atrial pacing of AVN fat pad simulation immediately after fibrin glue injection.
Figure 18:
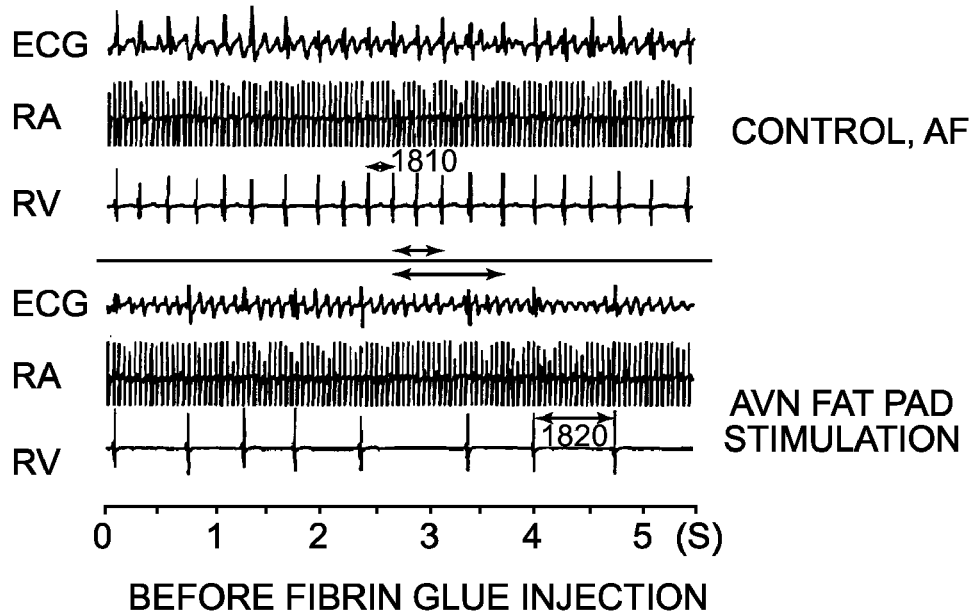
FIG. 18 is a graph showing in the time domain the impact on atrial fibrillation of AVN fat pad simulation before fibrin glue injection.
Figure 19:
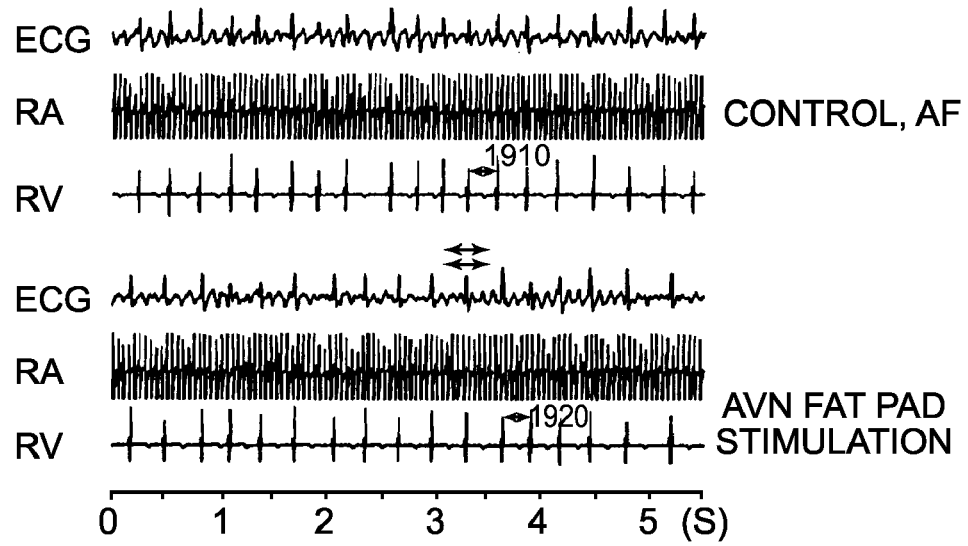
FIG. 19 is a graph showing in the time domain the impact on atrial fibrillation of AVN fat pad simulation immediately after fibrin glue injection.

The following results were observed. Electrical stimulation of the fat pads prior to fibrin glue injection resulted in various observable effects. FIG. 14 shows that before fibrin glue injection, electrical stimulation of the sinus node fat pad produced pronounced chronotropic effect; compare interval 1410 with interval 1420 to see prolongation of the cycle length. Similarly, FIG. 16 shows that before fibrin glue injection, electrical stimulation of the AV node fat pad produced clear dromotropic effect; compare relative timing of pulses 1610 and 1620 to see prolongation of the RA-RV interval. Moreover, FIG. 18 shows that during induced atrial fibrillation, the stimulation of the AV node fat pad resulted in strong reduction of the ventricular rate; compare intervals 1810 and 1820. However, these effects were not observed upon electrical stimulation of the fat pads immediately after injection of the fibrin glue. FIG. 15 shows that intervals 1510 and 1520 are essentially equal; compare FIG. 15 with FIG. 14. FIG. 17 shows that the relative timing of pulses 1710 and 1720 is essentially unchanged; compare FIG. 17 with FIG. 16. FIG. 19 shows that intervals 1910 and 1920 are essentially equal; compare FIG. 19 with FIG. 18.

Four weeks after the initial injections the experiments were repeated following the same protocol, and in addition vagal stimulation was also delivered through the cervical vagus. After the 4-week period all vagal effects were present.

EXPERIMENTAL EXAMPLE 2

In a clinical study, a type CM-1 fibrin sealant formulation was injected into the SA nodal and AV nodal fat pads for reducing the incidence of post-operative AF in patients undergoing low to moderate risk open chest surgery. The injection of the fibrin sealant is believed to have achieved temporary modification of the epicardial fat pads in patients undergoing low to moderate risk open chest surgery, thereby moderating the imbalance of the autonomic nervous system that typically occurs after surgical intervention and is a major determinant in post-op atrial fibrillation.

Eighteen human patients, fifteen of which were men, with a mean age of 66±8 years, a mean Euroscore of 4.1±2.6, and presenting for CABG and/or mitral valve surgery and with no previous history of AF were included in this study. SA and AV fat pads were defined using high frequency stimulation. CM-1 fibrin sealant formulation was injected into the defined fat pads during the planned surgical procedure. All patients underwent continuous cardiac telemetry for 96 hours postoperatively Holter was also obtained 14 and 30 days postoperatively. All 18 patients underwent successful injection of the CM-1 fibrin sealant formulation. Fourteen patients completed the 30 days, and sixteen patients completed the 14 days follow up. No major CM-1 fibrin sealant formulation related side effects were documented. Table 1 demonstrates the study results.

TABLE 1

| | |
|---|---|
| Patients | 18 |
| Mean EF (%) | 58 ± 11 |
| Combined CABG + mitral valve surgery | 2/18 (11%) |
| Post OP persistent AF requiring intervention (within 96 hours) | none |
| AF at discharge | none |
| Paroxysmal AF (>30 min duration) at any time post OP | 4/18 (22%) |
| Paroxysmal AF of any duration | 6/18 (33%) |
| Use of antiarrhythmic drug at discharge | 1/18 (5.5%) |

This study provides initial clinical evidence of the safety of CM-1 fibrin sealant formulation injected into the epicardial fat pads in patients undergoing low to moderate risk open chest surgery, and of the ability of CM-1 fibrin sealant formulation to prevent persistent post-op AF. Injections of CM-1 fibrin sealant formulation were observed to abolish the need for post operative intervention for treatment of AF by diminishing the incidence of persistent AF and shorting the duration of paroxysmal AF.

Figure 20:
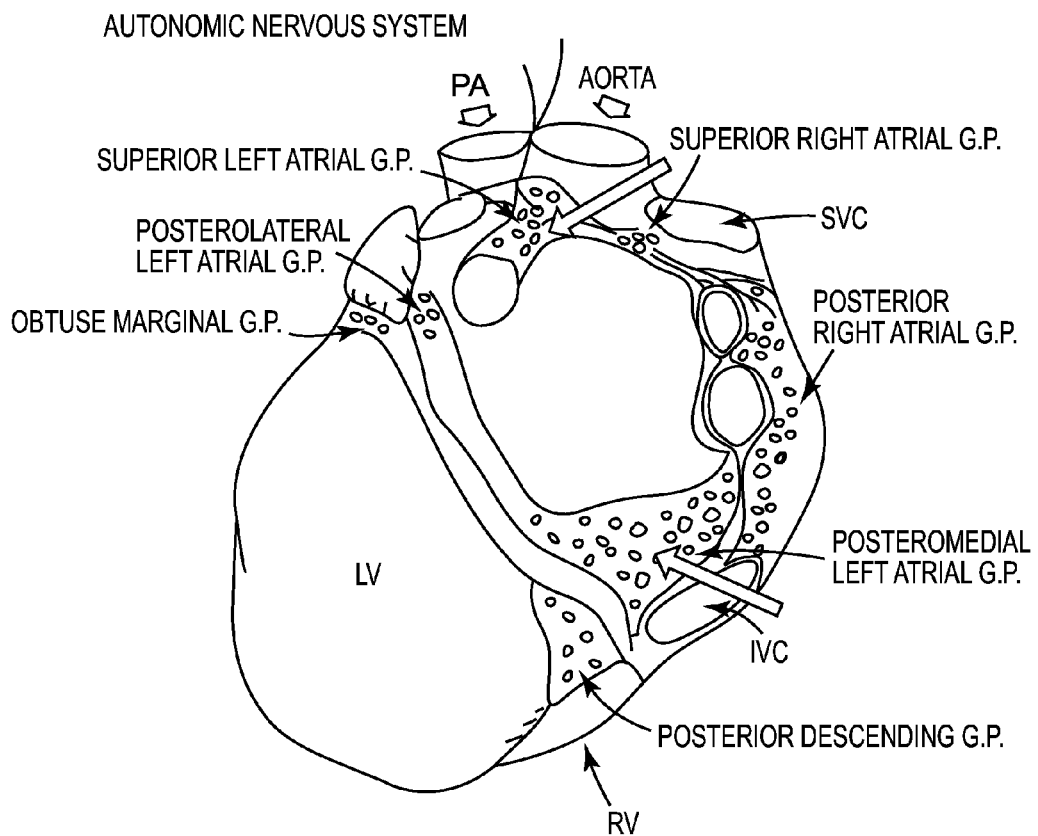
FIG. 20 is a plan view of the posterior heart, with various cardiac fat pad ganglionated plexuses identified.

FIG. 20 is a plan view of the posterior heart, with various cardiac fat pad ganglionated plexuses identified. The CM-1 fibrin sealant formulation was injected into the superior left atrial ganglionated plexuses and the posteromedial left atrial ganglionated plexus in fat pads respectively known as the sinoatrial nodal fat pad and the atrioventricular nodal fat pad, as indicated by the broad elongated arrows in the figure.

Figure 21:
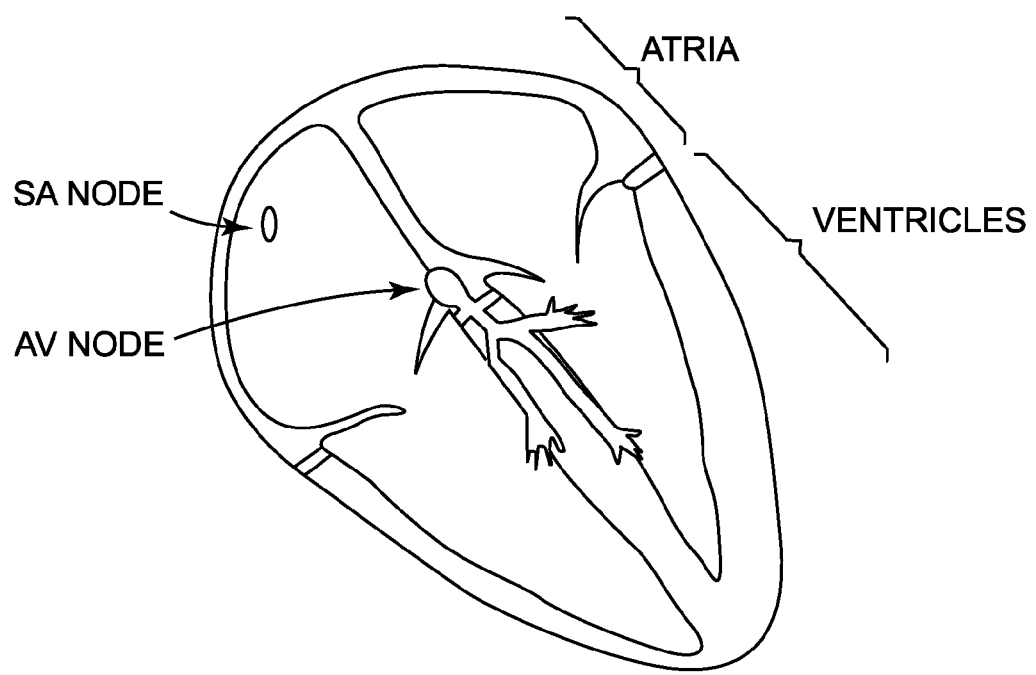
FIG. 21 is a cross-sectional view of the heart showing the locations of the SA node and the AV node.
Figure 22:
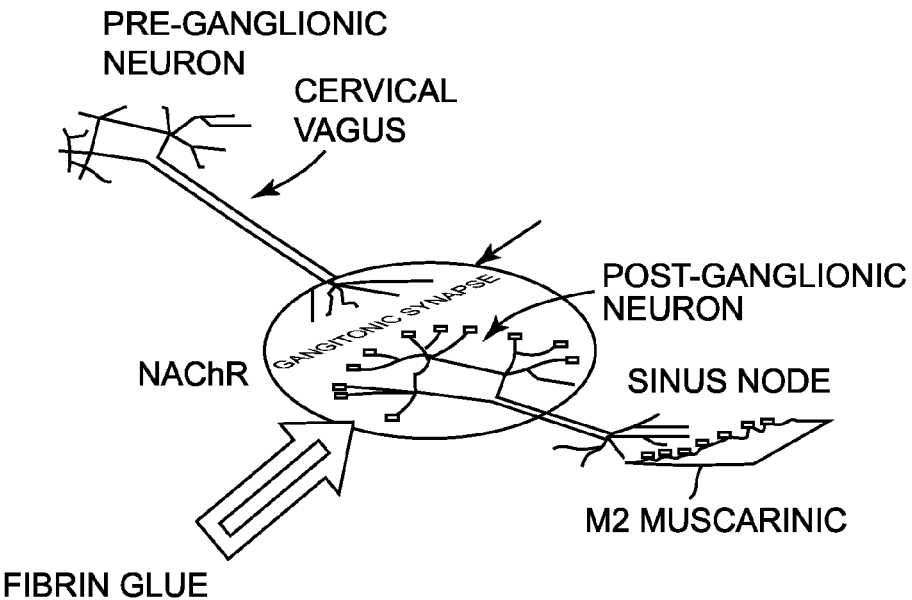
FIG. 22 is an exploded schematic view of the SA nodal fat pad.
Figure 23:
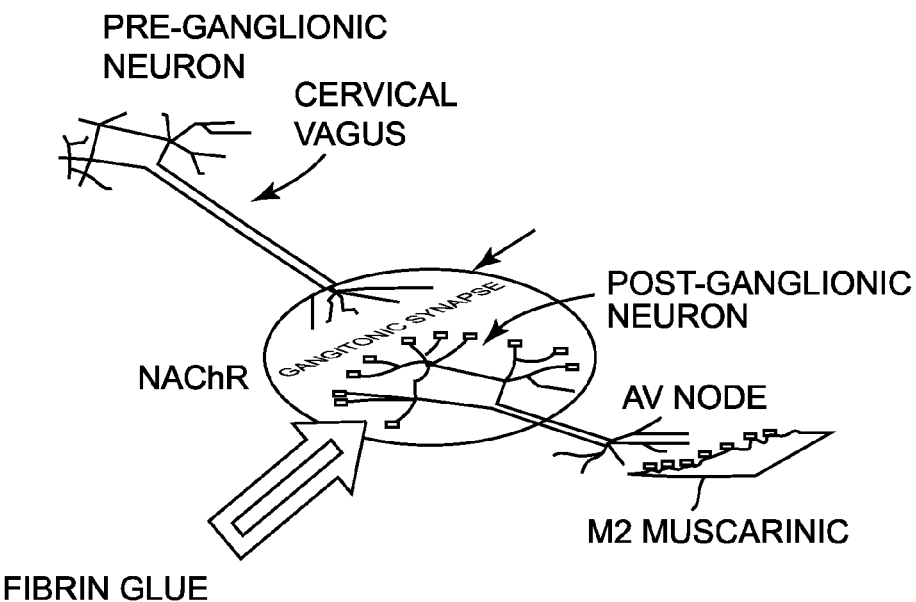
FIG. 23 is an exploded schematic view of the AV nodal fat pad.

FIG. 21 is a cross-sectional view of the heart showing the locations of the SA node and the AV node, FIG. 22 is an exploded schematic view of the SA nodal fat pad, and FIG. 23 is an exploded schematic view of the AV nodal fat pad. In each figure, a pre-ganglionic neuron of the cervical vagus is shown entering into the fat pad, and a post-ganglionic neuron is shown extending from the fat pad to one of the nodes, the SA node in FIG. 22 and the AV node in FIG. 23. Fibrin glue is injected into both the SA nodal fat pad and the AV nodal fat pad.

The protocol was for a phase I/II open-label, single dose (n=20) study. The patients involved were undergoing coronary artery bypass grafting surgery and presenting with a Euroscore of less than 5, that is, low to moderate risk patients. While many different types of fibrin sealant (glue) are suitable, the fibrin sealant used was Quixil™ human hemostatic sealant available from Omrix Biopharmaceuticals Inc. of New York, N.Y., USA. Quixil sealant is a one-to-one (1:1) ratio mixture of two biologically active components that contain fibrinogen precursor thrombin precursor respectively. A single injection was made into each of the anterior and posterior fat pads.

Figure 24:
FIG. 24 is a graph showing the R-R interval durations prior to fibrin sealant injection.

The procedure was as follows. During the planned CABG or valve replacement procedure, the surgeon identified the sinoatrial ("SA") nodal fat pad that is located at the right side of the superior vena cava and the level of the mid-portion of the anterior PA, and the atrioventricular ("AV") nodal fat pad that is located at the junction of inferior vena cava and the left atrium (IVC-LA). The location of each cardiac fat pad is confirmed by using a handheld electrical stimulation device, which provided a small current and when applied to the region of the cardiac fat pad caused a discernable (20% or more) reduction in heart rate to be observed. Sustained (20 seconds or more) electrical stimulation of the cardiac fat pad can result in a complete heart block which is immediately reversed upon cessation of the electrical stimulus. FIG. 24 is a graph showing the R-R interval durations prior to fibrin sealant injection. Prior to nerve stimulation, the R-R interval is 840 ms which corresponds to about 71 beats per minute ("bpm"). Nerve stimulation produced a pronounced chronontropic effect; following nerve stimulation, the R-R interval was prolonged to 1120 ms which corresponds to about 54 bpm. This procedure provided for an accurate placement of the location for injection of the CM-1 fibrin sealant formulation.

Figure 25:
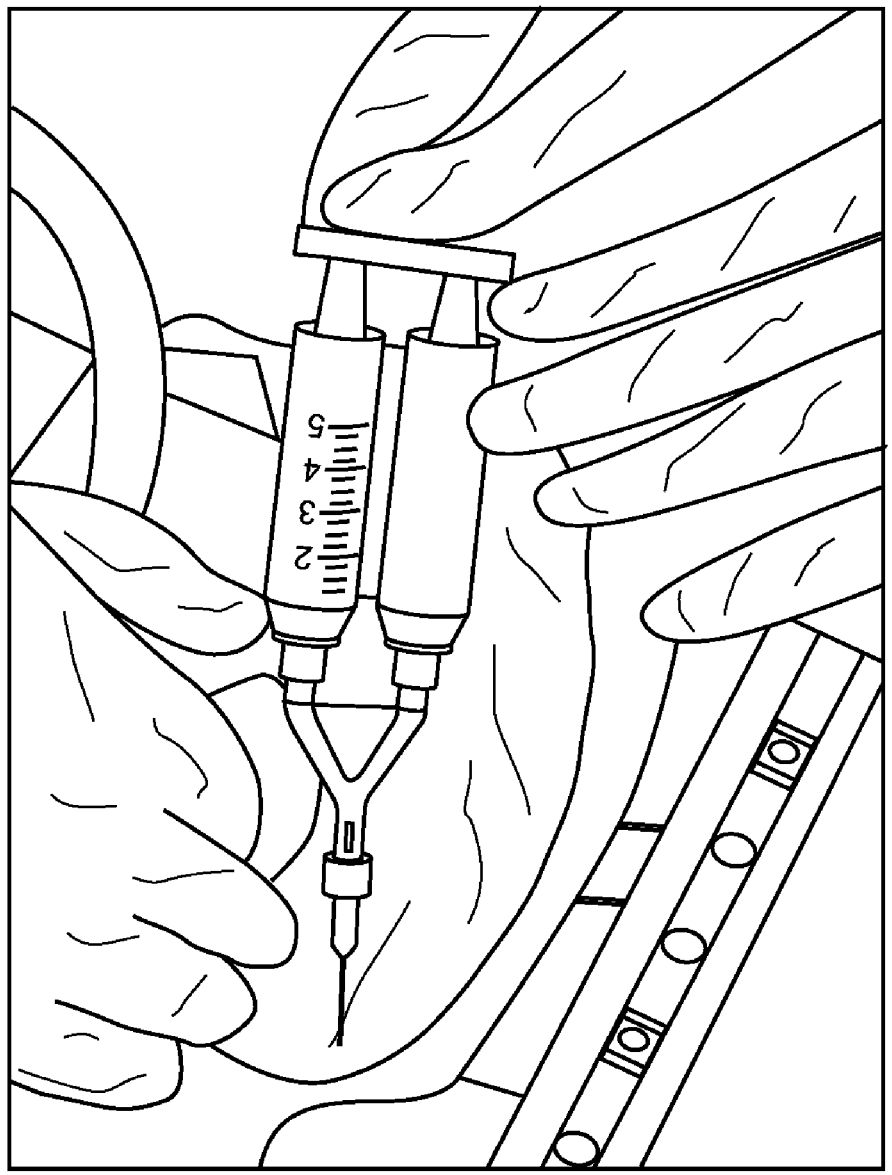
FIG. 25 is a plan view of a heart during a procedure, showing injection of the CM-1 fibrin sealant formulation.

FIG. 25 is a plan view of a heart during a procedure, showing injection of the CM-1 fibrin sealant formulation.

Figure 26:
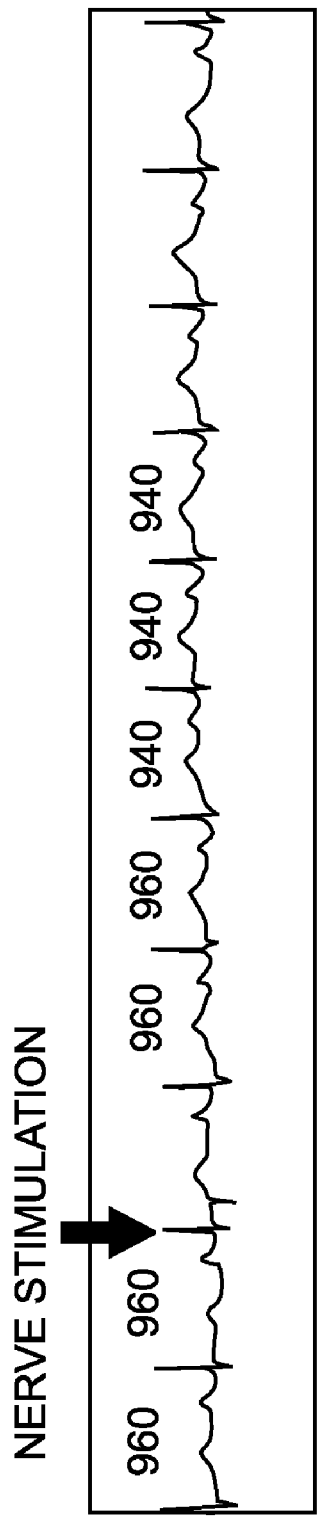
FIG. 26 is a graph showing R-R interval durations immediately after CM-1 fibrin sealant formation injection.

FIG. 26 is a graph showing R-R interval durations immediately after CM-1 fibrin sealant formation injection. A stimulation performed immediately after fibrin sealant injection had no effect on the R-R interval, which remained at 960 ms or about 63 bpm. This indicates that the fibrin sealant effectively blocked any effect of the stimulation on the autonomic ganglia.

The study endpoint assessment was as follows. All patients were monitored continuously with electrocardiographic (ECG) telemetry equipment, and a Holter monitor. The patients 24-hour reports were reviewed by a study physician daily to assess for any episode of AF. The end point of the study was the occurrence of AF lasting more than or equal to 30 minutes, or for any length of time requiring intervention due to symptoms such as chest pain, or hemodynamic compromise such as hypotension or heart failure, or the completion of the 30 day follow-up period.

The safety assessments were as follows. The safety and tolerability of the CM-1 fibrin sealant formulation was evaluated through an analysis of adverse experiences, clinical laboratory tests, electrocardiogram and physical examinations, echocardiograms, and Holter monitors.

The patient demographics were as follows. There were 20 patients of age 66 years plus or minus 8 years. Fifteen of the patients were male. The patients' EuroScore were 4.1 plus or minus 2.6. The percentage of patients with hypertension was 100%. The percentage of patients with chronic heart failure was 14%. The ejection fractions of the patients were 58 plus or minus 11. The percentage of patients requiring combined CAGB and valve procedures was 11%. The percentage of patients pre-operatively using Beta blockers was 61%.

FIG. 27 is a table showing the incidence of post-operative AF from a clinical perspective. Firm assessments are difficult to make because of the small numbers in an open label study, and of significant difference in methods for the various studies. Nonetheless, the values shown in FIG. 27 are useful for giving a perspective.

Figure 28:
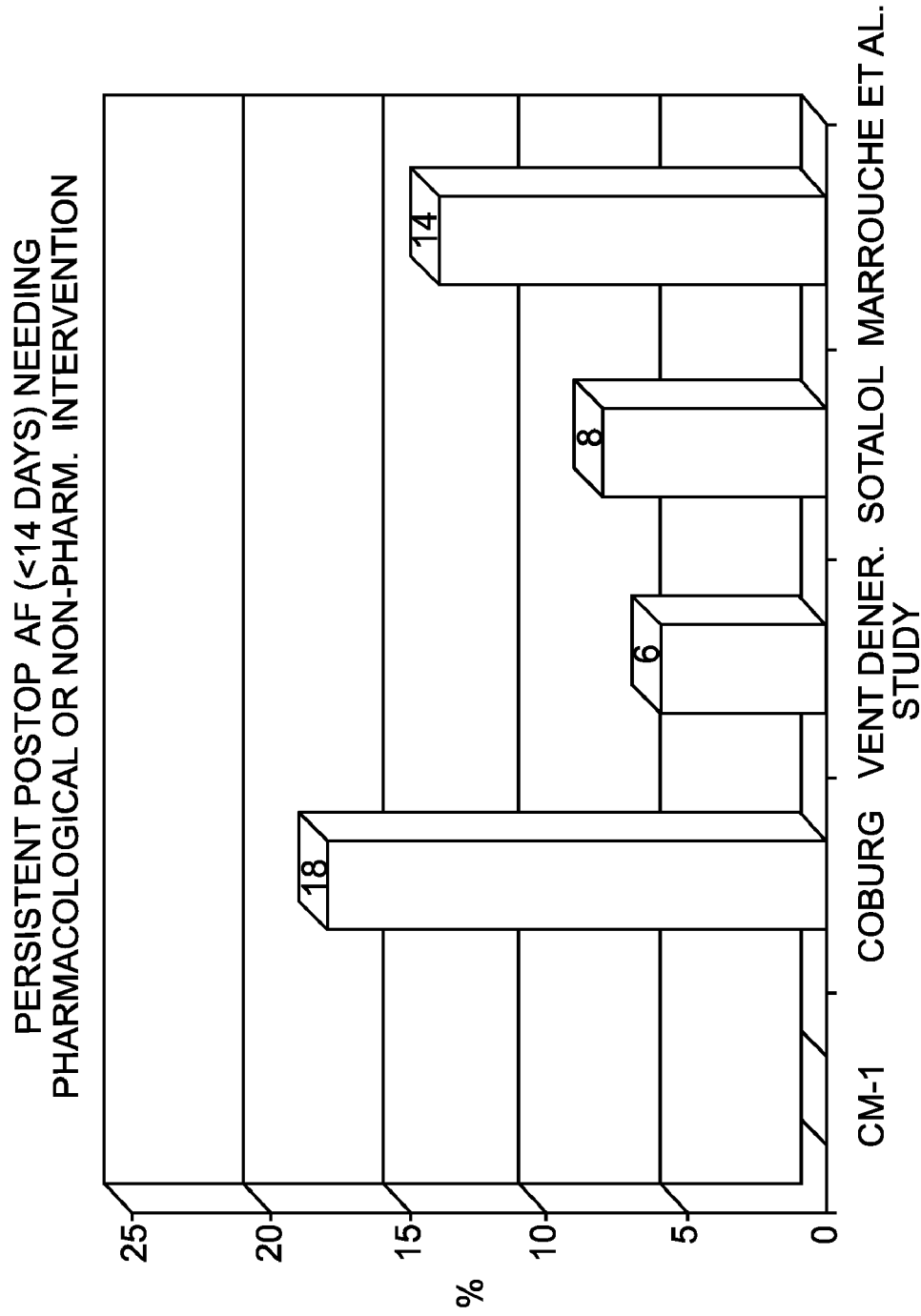
FIG. 28 is a bar chart showing incidents of persistent post operative AF requiring pharmacological or non-pharmacological intervention.

FIG. 28 is a bar chart showing incidents of persistent post operative AF (less than 14 days) requiring pharmacological or non-pharmacological intervention. There were no incidents with the use of the CM-1 fibrin sealant formulation. For the same reasons as FIG. 27, the bar chart in FIG. 28 is useful for giving a perspective.

Observations from the study are as follows. The technical feasibility of the CM-1 fibrin sealant formulation was confirmed by the successful administration of the CM-1 fibrin sealant formulation to all patients. No significant safety issues of note were observed, although there was the typical post-operative morbidity in that one death remote to the procedure did occur. Two of the twenty patients did have an event that qualified as sustained AF, defined by the standard definition of greater than 30 minutes or requiring intervention. The study employed strict end-point definition, AF through 30 days post-op. One of two qualifying events was self-terminating. One of two qualifying events was 2 weeks post-op. The effects of the CM-1 fibrin sealant formulation are likely gone by 2 weeks post administration. No patient experienced persistent atrial fibrillation requiring intervention during the immediate (96 hour) post-op period.

EXPERIMENTAL EXAMPLE 3

Alginate was injected into the SAN and AVN fat pads using a protocol similar to that used in Experimental Example 1. The injection site was confirmed by stimulation of the fat pads. The effect of the injected material was tested by applying cervical vagal stimulation. The observed result was the strong attenuation of the cervical vagal stimulation, suggesting that the injected material was effective over the short term to functionally inhibit neuronal signaling in autonomic ganglia contained in the fat pad.

The alginate formulation used was a self-gelling alginate available from the NovaMatrix Division of FMC BioPolymer of Drammen, Norway. This alginate has two components, a calcium component and a sodium alginate component, which are premixed in a single lumen, dual chamber delivery system. While the amount of alginate and proportions of the components may be varied as desired, 4.0 ml of alginate was used in this experiment, with a 4:1 ratio of the calcium component (3.2 ml) to the sodium alginate (0.8 ml). The two components were pre-mixed within the component vials using a valve set to allow the components to pass from vial to vial, and were injected into the fat pad through a single lumen with the valve set in a second position.

The cervical vagal stimulation used impulses at a frequency of 20 Hertz (50 msec intervals) and a duration of 0.5 ms. Two different amplitude levels were used, an moderate level of 4 mA and a very strong level of from 6 mA to 7 ma.

Figure 29:
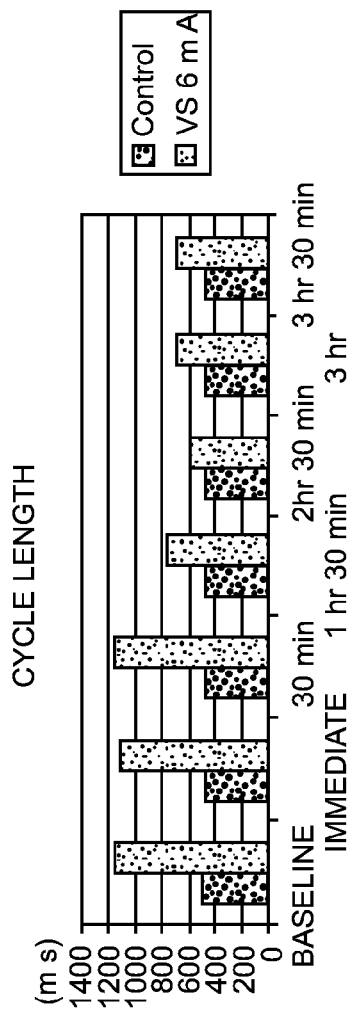
FIG. 29 is a graph that shows cycle length for dog 1.
Figure 30:
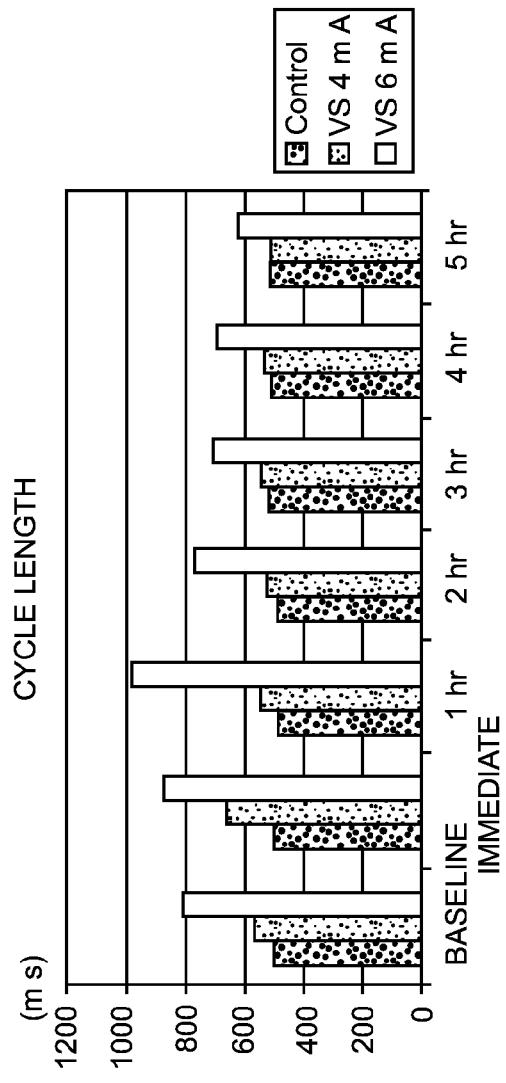
FIG. 30 is a graph that shows cycle length for dog 2.

FIGS. 29 and 30 are graphs that show cycle length. Cycle length essentially tests the functional capability of the sinoatrial nodal fat pad, which preferentially innervates the sinoatrial node. The baseline measurements prior to injection show the sinus cycle of about 500 ms. As the vagal stimulation is increased, the cycle length is prolonged. Within about two hours after injection, the moderate vagal stimulation ceases to have any significant effect on the cycle length, indicating functional impediment of neuronal signaling in autonomic ganglia contained in the SAN fat pad. The strong vagal stimulation continues to have some effect, although the effect tended to decreased over time.

Figure 31:
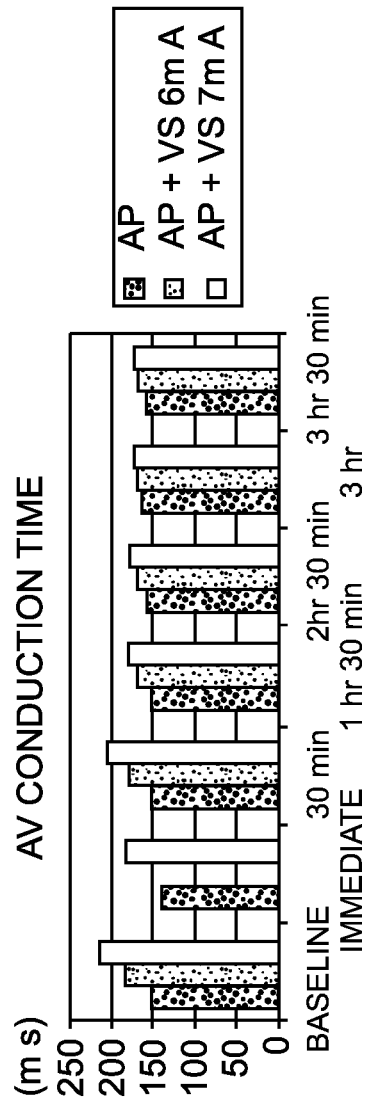
FIG. 31 is a graph that shows AV conduction time for dog 1.
Figure 32:
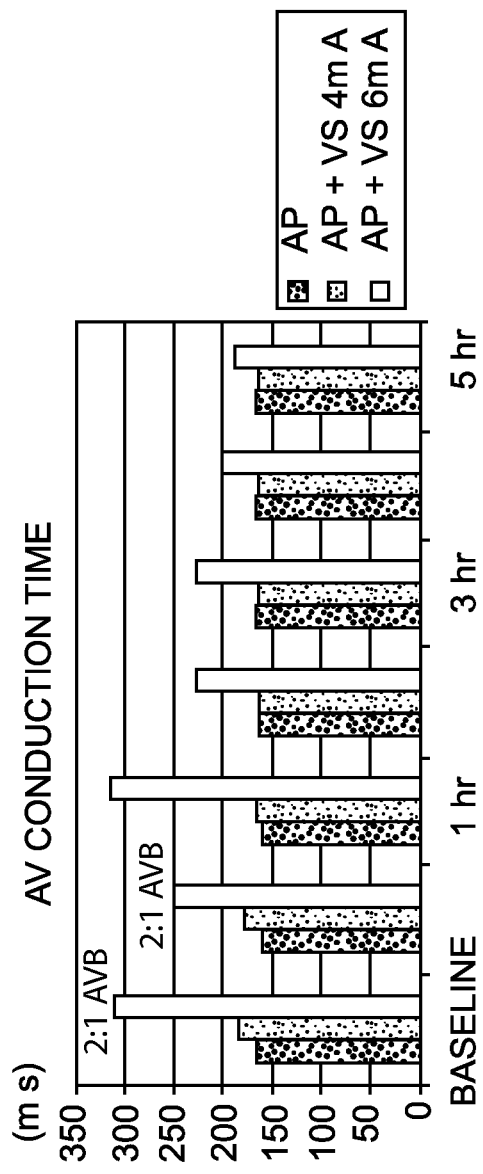
FIG. 32 is a graph that shows AV conduction time for dog 2.

FIGS. 31 and 32 are graphs that show AV conduction time. AV conduction time essentially tests the functional capability of the atrioventricular nodal fat pad, which preferentially innervates the atrioventricular node which entirely determines AVN conduction time. An external pacemaker was used to pace the atrium at 150 bpm, which overruled the vagus input. The baseline measurements prior to injection for dog 2, for example, shows that strong vagal stimulation causes a 2:1 AVB (AV block), i.e. every other heart beat was fully blocked. However, after only one hour (dog 2), moderate vagal stimulation had no effect and strong vagal stimulation had a significantly reduced effect. This indicates functional impediment of neuronal signaling in autonomic ganglia contained in the AVN fat pad.

Figure 33:
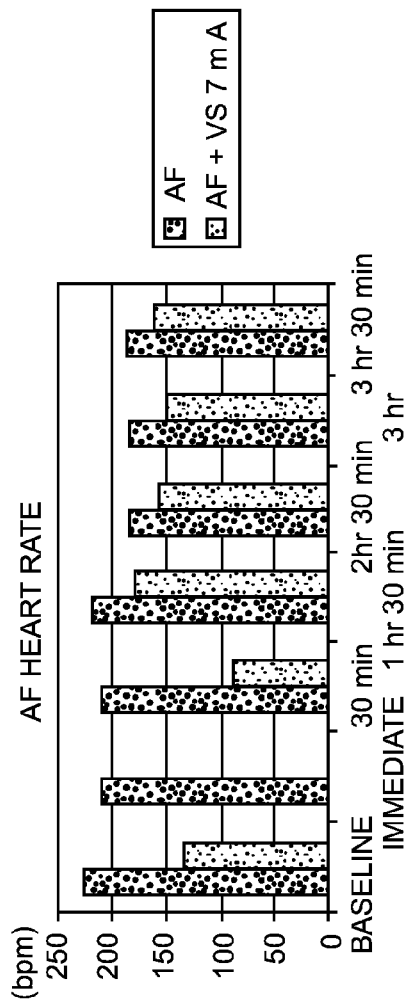
FIG. 33 is a graph that shows heart rate when vagal stimulation is applied after induced atrial fibrillation, for dog 1.
Figure 34:
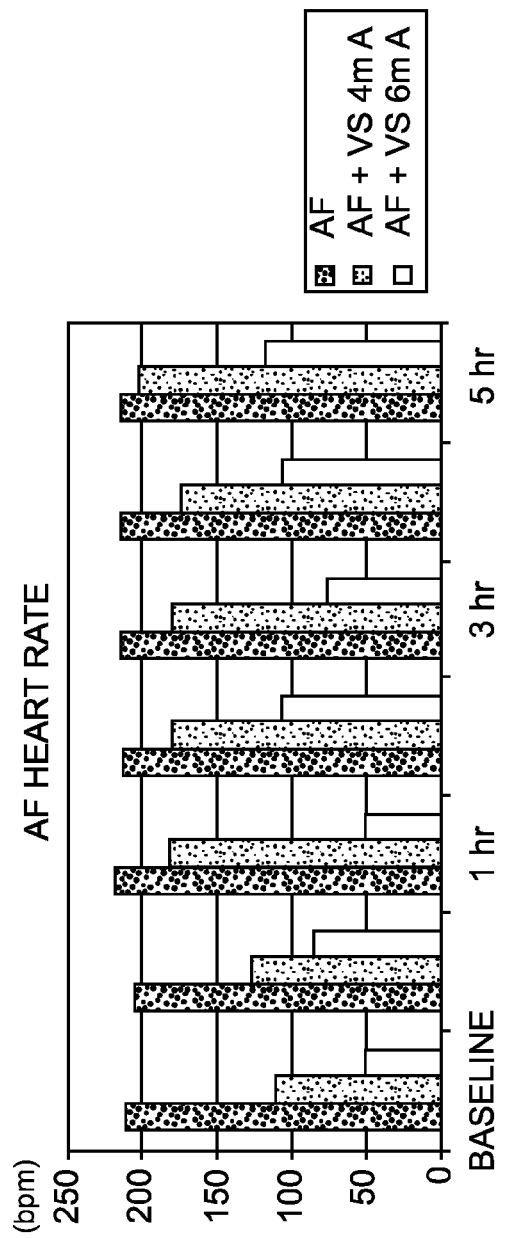
FIG. 34 is a graph that shows heart rate when vagal stimulation is applied after induced atrial fibrillation, for dog 2.

FIGS. 33 and 34 are graphs that show heart rate when vagal stimulation is applied after induced atrial fibrillation. During AF the sinus node is essentially non-responsive to vagus nerve stimulation. Heart rate essentially tests the functional capability of the atrioventricular nodal fat pad, which preferentially innervates the atrioventricular node. The baseline measurements prior to injection for dog 2, for example, shows that vagal stimulation is effective for reducing the heart rate. However, after injection the vagal stimulation becomes generally less effective. This indicates functional impediment of neuronal signaling in autonomic ganglia contained in the AVN fat pad.

The specific values of cycle length in dogs 1 and 2 were as shown in Table 2 and Table 3, which follow.

TABLE 2

| | Cycle length (ms) | |
| --- | --- | --- |
| | Control | VS 6 mA |
| Baseline | 506 | 1157 |
| Immediate | 450 | 1100 |
| 30 min | 464 | 1155 |
| 1 hr 30 min | 462 | 756 |
| 2 hr 30 min | 469 | 593 |
| 3 hr | 464 | 653 |
| 3 hr 30 min | 474 | 678 |

TABLE 3

| | Cycle length (ms) | | |
| --- | --- | --- | --- |
| | Control | VS 4 mA | VS 6 mA |
| Baseline | 500 | 564 | 806 |
| Immediate | 500 | 670 | 871 |
| 1 hr | 487 | 544 | 990 |
| 2 hr | 490 | 532 | 763 |
| 3 hr | 520 | 538 | 703 |
| 4 hr | 515 | 530 | 684 |
| 5 hr | 513 | 512 | 622 |

The specific values of AV conduction time in dogs 1 and 2 were as shown in Table 4 and Table 5, which follow.

TABLE 4

| | AV conduction time (ms) | | |
|---|---|---|---|
| | AP | AP + VS 6 mA | AP + VS 7 mA |
| Baseline | 153 | 182 | 213 |
| Immediate | 140 | | 180 |
| 30 min | 155 | 176 | 205 |
| 1 hr 30 min | 153 | 168 | 180 |
| 2 hr 30 min | 157 | 166 | 178 |
| 3 hr | 162 | 168 | 170 |
| 3 hr 30 min | 157 | 165 | 174 |

TABLE 5

| | AV conduction time (ms) | | | |
|---|---|---|---|---|
| | AP | AP + VS 4 mA | AP + VS 6 mA | AV block |
| Baseline | 163 | 185 | 312 | 2:1 AVB |
| Immediate | 162 | 177 | 250 | 2:1 AVB |
| 1 hr | 163 | 166 | 316 | (−) |
| 2 hr | 163 | 163 | 227 | (−) |
| 3 hr | 166 | 163 | 229 | (−) |
| 4 hr | 164 | 163 | 200 | (−) |
| 5 hr | 165 | 163 | 190 | (−) |

The specific values of AF heart rate in dogs 1 and 2 were as shown in Table 6 and Table 7, which follow.

TABLE 6

| | AF Heart Rate (bpm) | |
|---|---|---|
| | AF | AF + VS 7 mA |
| Baseline | 225 | 132 |
| Immediate | 210 | |
| 30 min | 210 | 90 |
| 1 hr 30 min | 220 | 180 |
| 2 hr 30 min | 185 | 156 |
| 3 hr | 185 | 150 |
| 3 hr 30 min | 190 | 165 |

TABLE 7

| | AF Heart Rate (bpm) | | |
|---|---|---|---|
| | AF | AF + VS 4 mA | AF + VS 6 mA |
| Baseline | 210 | 108 | 48 |
| Immediate | 204 | 126 | 84 |
| 1 hr | 216 | 180 | 52 |
| 2 hr | 214 | 180 | 108 |
| 3 hr | 216 | 180 | 78 |
| 4 hr | 216 | 174 | 108 |
| 5 hr | 218 | 204 | 120 |

EXPERIMENTAL EXAMPLE 4

A further study was performed to compare the effects of direct injection of different formulations of alginate, fibrin sealant and Polyethylene Glycol ("PEG") into five fat pads, specifically, the sinus node fat pad, the AV node fat pad, the left superior pulmonary vein ("LSPV") fat pad, the left inferior pulmonary vein ("LIPV") fat pad, and the Ligament of Marshall fat pad. Fourteen dogs were enrolled in the study. An open chest procedure was used. The non-ablative test agents were directly injected into the fat pads, and an evaluation was performed on the effects of the various test agents on sinus cycle length ("SCL"), AF threshold, and RR interval during atrial fibrillation. The evaluation was performed by direct stimulation of the fat pads using stimulation at 20 Hz and variable current ranging from 0.1 mA to 10 mA. The evaluation was performed one hour after injection and at 5-8 days post injection. The animals were sacrificed and a histologic evaluation performed.

The twenty-four dogs were studied in seven groups. The study of alginate Formulation 1 was performed on three animals, the study of alginate Formulation 2 was performed on four animals with one casualty, the study of alginate Formulation 5 was performed on two animals, the study of Duraseal was performed on four animals with one casualty, the study of Coseal was performed on five animals with two casualties, and the study of TisSeel was performed on three animals. A saline group of three animals was included. None of the casualties were believed to be related to the test article. Three of the casualties were intraoperative, possibly due to an ischemic event and one casualty was due to pneumothorax.

Table 8 below shows sinus cycle length data, expressed as a percentage of the maximum prolongation obtained during follow-up compared to baseline following fat pad stimulation. The percentage of reduction in the response to fat pad stimulation is categorized in three groups, namely significant reduction ($\geqq$90%), moderate reduction ($\geqq$40% & <90%), and discreet reduction (<40%). Animal deaths and cases without response to fat pad stimulation at baseline are excluded.

TABLE 8

| GROUP | <40% | $\geqq$40% & <90% | $\geqq$90% | # FAT PADS ANALYZED |
|---|---|---|---|---|
| Formulation 1 | 0 (0%) | 1 (25%) | 3 (75%) | 4 |
| Formulation 2 | 0 (0%) | 1 (100%) | 0 (0%) | 1 |
| Formulation 5 | 1 (25%) | 0 (0%) | 3 (75%) | 4 |
| Duraseal | 0 (0%) | 1 (33.3%) | 2 (66.7%) | 3 |
| CoSeal | 0 (0%) | 0 (0%) | 2 (100%) | 2 |
| TisSeel | 2 (33.3%) | 2 (33.3%) | 2 (33.3%) | 6 |
| Saline | 3 (75%) | 1 (25%) | 0 (0%) | 4 |

Table 9 below shows AF threshold data during fat pad stimulation at baseline and at follow-up., determined as the variation in energy necessary to induce AF comparing follow-up and baseline. The data is categorized in three groups, namely discreet increase in threshold (<2 mA), moderate increase in threshold (>2 mA), and no induction at follow-up. Animal deaths and cases without response to fat pad stimulation at baseline are excluded.

TABLE 9

| GROUP | <2 mA | >2 mA | No Induction | # FAT PADS ANALYZED |
|---|---|---|---|---|
| Formulation 1 | 2 (13.3%) | 6 (40.0%) | 7 (46.7%) | 15 |
| Formulation 2 | 3 (20.0%) | 8 (53.3%) | 4 (26.7%) | 15 |
| Formulation 5 | 2 (18.2%) | 7 (63.6%) | 2 (18.2%) | 11 |
| Duraseal | 0 (0.0%) | 5 (35.7%) | 9 (64.3%) | 14 |
| CoSeal | 2 (14.3%) | 2 (14.3%) | 10 (71.4%) | 14 |
| TisSeel | 6 (40.0%) | 2 (13.3%) | 7 (46.7%) | 15 |
| Saline | 10 (66.7%) | 4 (26.7%) | 1 (6.7%) | 15 |

As indicated by the data, all agents tested can blunt neuronal signaling in ganglia contained in the fat pad and protect against neurally-induced AF induction.

Identification of Site of Injection on the Fat Pads

To accurately identify the site on the fat pad for injection of the non-ablative agent, a stimulator is used to stimulate the autonomic ganglia contained in the fat pads. Stimulation may be applied in any suitable manner. In one approach, stimulation may be applied to the fat pads through bipolar plate electrodes. As reported in Experimental Example 1, electrical stimulation of the fat pads prior to fibrin glue injection results in various observable effects, most notably prolongation of the cycle length, prolongation of the RA-RV interval, and strong reduction of the ventricular rate during atrial fibrillation. In another approach, stimulation may be applied by a handheld unit. As reported in Experimental Example 2, high frequency stimulation may be applied to the fat pads by using a handheld electrical stimulation device, which provides a small current and when applied to the region of the cardiac fat pad near the autonomic ganglia, and causes a discernable (20% or more) reduction in heart rate to be observed. Sustained (20 seconds or more) electrical stimulation of the cardiac fat pad can result in a complete heart block which is immediately reversed upon cessation of the electrical stimulus. Nerve stimulation produced a pronounced chronontropic effect; following nerve stimulation, the R-R interval was prolonged. In another approach, stimulation may be applied through a catheter. The catheter of FIG. 6 includes lead wires 620 and 650, which may be connected to stimulation electrodes for applying stimulation energy to the fat pads. When the stimulation electrodes are near autonomic ganglia contained in the fat pads, clear chronotropic and dromotropic effects on the heart are observable. The identified location is suitable for injection of non-ablative agent. In another approach, suitable electrodes are mounted at the end of an injection needle, so that identifying the target site on the fat pad and injecting the non-ablative agent may be done in one continuous action.

Various arrangements of stimulator electronics and electrodes are possible. The stimulator electronics may be contained in a reusable housing and the electrode may be single use and removable. The stimulator electronics may be contained in a reusable housing and the electrode may be removable and capable of being sterilized for multiple use. The stimulator electronics and the electrodes together may form a handheld unit, with the electrodes being permanently attached or removable as desired. The handheld unit may be disposable or reusable. The stimulator electronics may be remote from the heart and the electrodes may be connected to the stimulator electronics by wires.

Figure 35:
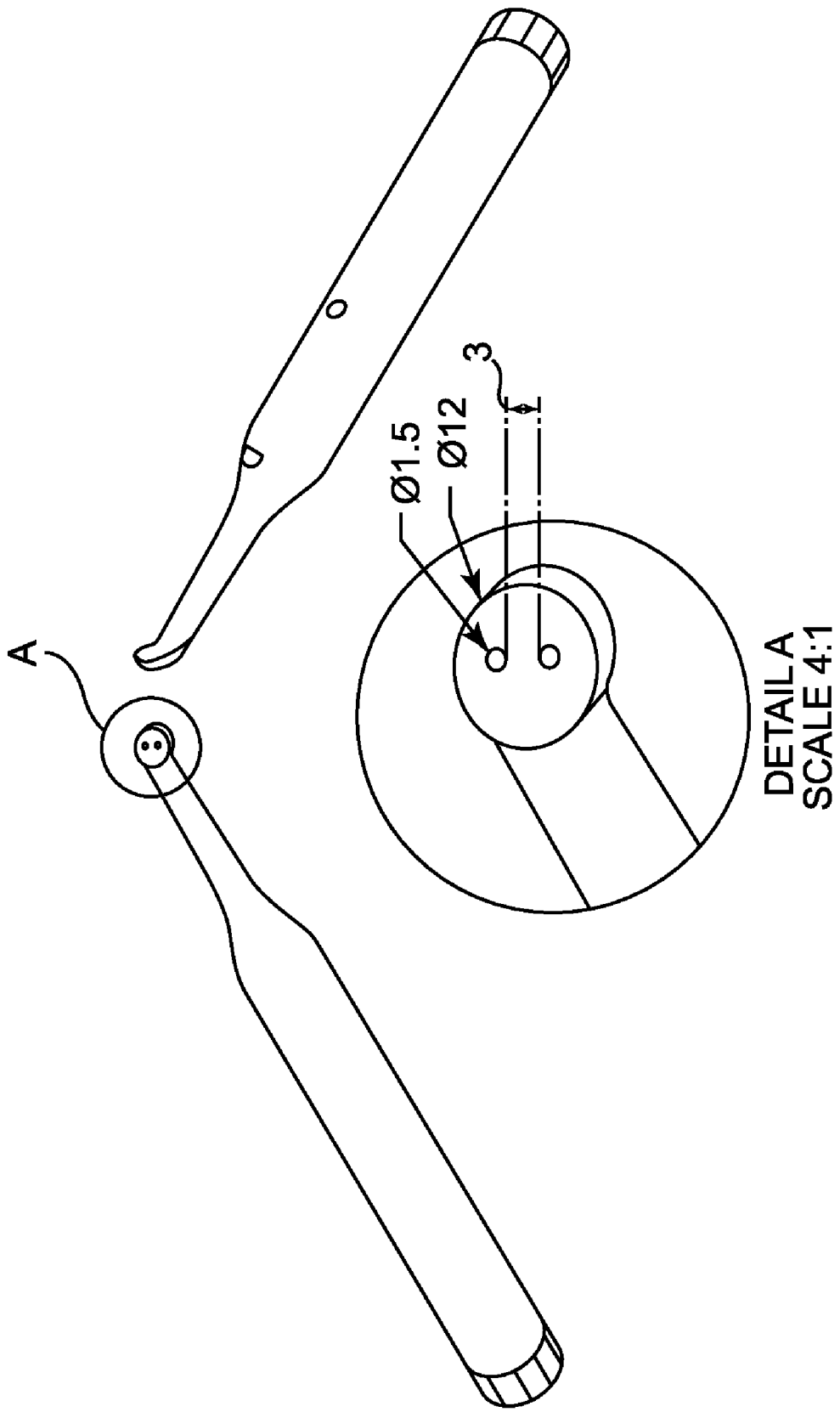
FIG. 35 is a plan view of an illustrative handheld stimulator suitable for locating target sites on the fat pads.

FIG. 35 is a plan view of an illustrative handheld stimulator suitable for locating target sites on the fat pads. The elongated body contains the electronics and battery for generating the stimulation. The electrode head has a planar face that is angled 30 degrees relative to the elongated body of the stimulator. The electrode head is 12 mm in diameter, and contains two electrodes in a bipolar configuration which project from the planar face and are 1.5 mm in diameter and spaced apart 3 mm. While FIG. 35 shows a bipolar electrode configuration, other electrode configurations such as mono-polar may be used if desired. Preferably, the stimulator of FIG. 35 is single use.

Kit

Figure 36:
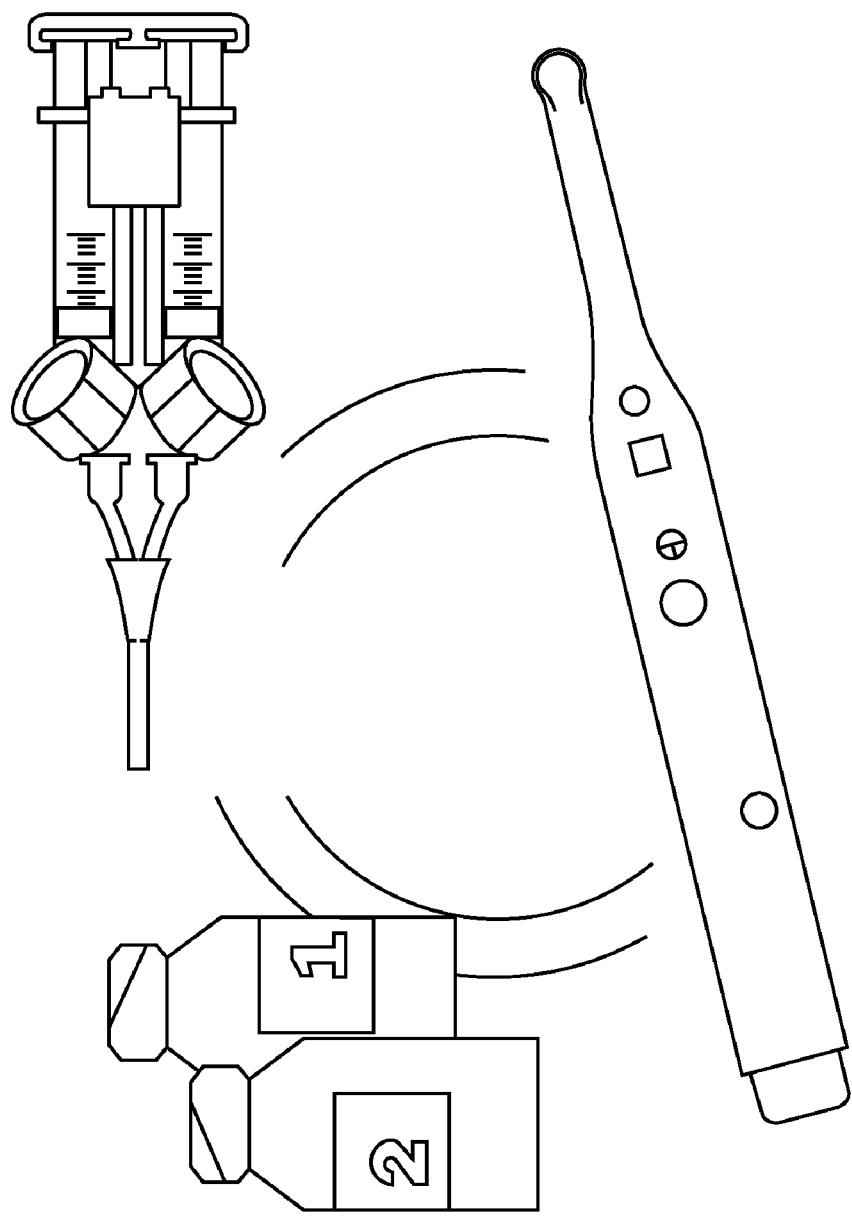
FIG. 36 is a schematic drawing of the components of a kit for achieving post-operative control of atrial fibrillation by temporary modification of neuronal signaling through the fat pads of the heart.
Figure 37:
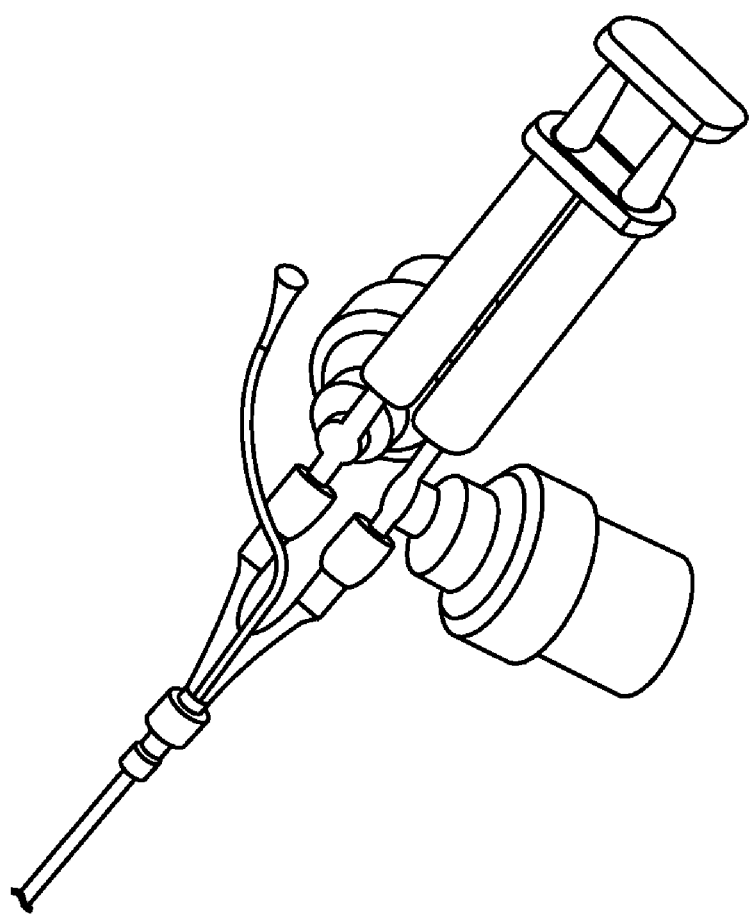
FIG. 37 is a pictorial view of a dual component delivery system.

FIG. 36 is a schematic drawing of the components of a kit for achieving post-operative control of atrial fibrillation by temporary modification of neuronal signaling through the fat pads of the heart. The kit includes any suitable non-ablative agent, illustrative a fibrin sealant such as the two components of the Quixil human hemostatic sealant in respective vials; any suitable agent delivery device such as the fibrin sealant applicator for fat pad injection available from Plasmed Ltd. of Tel Aviv, Israel (shown pictorially with vials installed in FIG. 37); and any suitable stimulator and stimulation electrodes. Illustratively, the stimulator with integrated electrodes of FIG. 35 is shown.

Although the stimulator shown in FIG. 35 is single use, a suitable stimulator may include a reusable body section housing the electronics, and a single use electrode section. Where a reusable stimulator electronics section is sold separately, a suitable kit may include the single use electrode section rather than the entirely stimulator.

The description of the invention including its applications and advantages as set forth herein is illustrative and is not intended to limit the scope of the invention, which is set forth in the claims. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

What is claimed is:

1. A method of treating cardiac arrhythmia in a heart of a patient comprising:
   preparing a source of non-ablative agent that is effective for modifying neuronal signaling by nerve tissue of the autonomic nervous system;
   electrically stimulating a cardiac fat pad to locate a target site on the cardiac fat pad in proximity to autonomic ganglia therein, the autonomic ganglia being a part of the autonomic nervous system; and
   delivering a therapeutically effective amount of the non-ablative agent from the source to the target site.

2. The method of claim 1 wherein the stimulation step comprises:
   stimulating autonomic ganglia contained in an atrioventricular nodal ("AVN") fat pad of the heart to identify an AVN fat pad target site; and
   stimulating autonomic ganglia contained in a sinoatrial nodal ("SAN") fat pad of the heart to identify an SAN fat pad target site; and
   wherein the delivering step comprises delivering a therapeutically effective amount of the non-ablative agent from the source to the AVN fat pad target site and to the SAN fat pad target site.

3. The method of claim 1 further comprising performing coronary artery bypass graft surgery in open chest surgery, wherein the delivering step comprises delivering the therapeutically effective amount of the non-ablative agent from the source to the target site during the open chest surgery.

4. The method of claim 1 further comprising performing mitral valve surgery in open chest surgery, wherein the delivering step comprises delivering the therapeutically effective amount of the non-ablative agent from the source to the target site during the open chest surgery.

5. The method of claim 1 wherein the delivering step comprises delivering the therapeutically effective amount of the non-ablative agent from the source to the target site during a percutaneous translumenal procedure.

6. The method of claim 1 wherein the delivering step comprises delivering the therapeutically effective amount of the non-ablative agent from the source to the target site during a transthoracic minimally invasive procedure.

7. The method of claim 1 wherein the non-ablative agent comprises a polymer.

8. The method of claim 7 wherein the polymer is fibrin glue.

9. The method of claim 7 wherein the polymer is alginate.

10. The method of claim 7 wherein the polymer is polyethylene glycol.

11. The method of claim 1 wherein the non-ablative agent comprises living cells.

12. The method of claim 11 wherein the non-ablative agent comprises fibroblasts.

13. The method of claim 1 wherein the non-ablative agent comprises a neurotoxin.

14. The method of claim 13 wherein the neurotoxin is Botulinum Type A.

15. The method of claim 1 wherein the non-ablative agent comprises growth factor.

16. The method of claim 15 wherein the growth factor is fibroblast growth factor.

17. The method of claim 1 wherein the non-ablative agent is selected from the group consisting of fibrin glue, collagen, alginate, polyethylene glycol, precursors and/or derivatives of the foregoing, and combinations of two or more of the foregoing.

* * * * *